(12) United States Patent
Wesche et al.

(10) Patent No.: US 7,235,635 B2
(45) Date of Patent: Jun. 26, 2007

(54) IRAK-4: COMPOSITIONS AND METHODS OF USE

(75) Inventors: Holger Wesche, San Francisco, CA (US); Shyun Li, Fremont, CA (US)

(73) Assignee: Amgen Inc., Thousand Oaks, CA (US)

( * ) Notice: Subject to any disclaimer, the term of this patent is extended or adjusted under 35 U.S.C. 154(b) by 56 days.

(21) Appl. No.: 10/990,276

(22) Filed: Nov. 15, 2004

(65) Prior Publication Data

US 2005/0255549 A1    Nov. 17, 2005

Related U.S. Application Data

(62) Division of application No. 09/759,595, filed on Jan. 11, 2001, now Pat. No. 6,818,419.

(51) Int. Cl.
*C07K 14/00* (2006.01)
*C07K 14/705* (2006.01)
*C12N 9/00* (2006.01)

(52) U.S. Cl. ............ 530/350; 435/69.1; 435/183

(58) Field of Classification Search ............... None
See application file for complete search history.

(56) References Cited

U.S. PATENT DOCUMENTS 6,440,663 B1 *   8/2002   Scanlan et al. ............ 435/6

FOREIGN PATENT DOCUMENTS

| WO | WO 98/44113 | 10/1998 |
|---|---|---|
| WO | WO 99/27112 | 6/1999 |
| WO | WO 99/60100 | 11/1999 |
| WO | WO 00/20587 | 4/2000 |
| WO | WO 00/73801 | 12/2000 |

OTHER PUBLICATIONS

Stryer, Ed., Biochemistry, Second Edition, W.H. Freeman and Co., 1981, Chapter 5, pp. 87-101.*
Bowie et al., 1990, Science 247:1306-1310.*
Wells, 1990, Biochemistry 29:8509-8517.*
Ashkenazi et al., PNAS Sep. 1990 87:7150-7154.*
Scanlan et al., 1999 Int J Cancer: 83, 456-464.*
Baeuerle et al., *Ann. Rev. Immunol.*, 12:141-179 (1994).
Cao et al., *Nature*, 383:443-446 (1996).
Cao et al., *Science*, 271:1128-1131 (1996).
Dinarello, *Cytokine & Growth Factor Rev.*, 8(4):253-265 (1997).
Feinstein et al., *TIBS*, 20:342-344 (1995).
Greenfeder et al., *J. Biol. Chem.*, 270(23):13757-13765 (1995).
Grilli et al., *Int. Rev. Cytol.*, 143:1-62 (1993).
Kanakaraj et al., *J. Exp. Med.*, 18(12)7:2073-2079 (1998).
Kanakaraj et al., *J. Exp. Med.*, 189(7):1129-1138 (1999).
Lee et al., *J. Clin. Pharmacol.*, 38:981-993 (1998).
Lenardo et al., *Cell*, 58:227-229 (1989).
Misteli et al., *Nature Biotechnology*, 15:961-964 (1997).
Muzio et al., *Science*, 278:1612-1615 (1997).
Scanlan et al., Accession No. AF=155118, XP-002168129, Jan. 5, 2000.
Scanlan et al., *Int. J. Cancer*, 83:456-464 (1999).
Schindler et al., *Mol. Cell Biol.*, 14(9):5820-5831 (1994).
Thomas et al., *J. Immunol.*, 163:978-984 (1999).
Voet et al., *Biochemistry*, John Wiley & Sons, Inc., pp. 126-128 and 228-234 (1990).
Wesche et al., *Immunity*, 7:837-847 (1997).
Wesche et al., *J. Biol. Chem.*, 274:19403-19410 (1999).
Yang et al., *J. Immunol.*, 163:639-643 (1999).
Yeh al., *Immunity*, 7:715-725 (1997).

* cited by examiner

*Primary Examiner*—Marianne P. Allen
*Assistant Examiner*—Cherie Woodward
(74) *Attorney, Agent, or Firm*—Jones Day

(57) ABSTRACT

The present invention provides nucleic acids and polypeptides for IRAK-4, a novel member of the IRAK family of protein kinases. Members of the IRAK family are indispensable signal transducer for members of the IL-1R/Toll family of transmembrane receptors, including IL-1 receptors, IL-18 receptors and LPS receptors. IRAK-4 sequences from human and mouse are provided, as are methods for identifying compounds useful in the treatment or prevention of inflammatory diseases.

3 Claims, 11 Drawing Sheets

```
           10              20              30              40
MNK PIT PST YVR CLN VGL IRK LSD FID PQE GWK KLA VAI KKP 50              60              70              80
SGD DRY NQF HIR RFE ALL QTG KSP TSE LLF DWG TTN CTA GDL 90             100             110             120
VDL LIQ NEF FAP ASL LLP DAV PKT ANT LPS KEA ITV QQK QMP 130             140             150             160
FCD KDR TLM TPV QNL EQS YMP PDS SSP ENK SLE VSD TRF HSF 170             180             190             200             210
SFY ELK NVT NNF DER PIS VGG NKM GEG GFG VVY KGY VNN TTV 220             230             240             250
AVK KLA AMV DIT TEE LKQ QFD QEI KVM AKC QHE NLV ELL GFS 260             270             280             290
SDG DDL CLV YVY MPN GSL LDR LSC LDG TPP LSW HMR CKI AQG 300             310             320             330
AAN GIN FLH ENH HIH RDI KSA NIL LDE AFT AKI SDF GLA RAS 340             350             360             370
EKF AQT VMT SRI VGT TAY MAP EAL RGE ITP KSD IYS FGV VLL 380             390             400             410             420
EII TGL PAV DEH REP QLL LDI KEE IED EEK TIE DYI DKK MND 430             440             450             460
ADS TSV EAM YSV ASQ CLH EKK NKR PDI KKV QQL LQE MTA S*
```

FIG. 1.

```
              10                  20                  30                  40
ATG AAC AAA CCC ATA ACA CCA TCA ACA TAT GTG CGC TGC CTC
 M   N   K   P   I   T   P   S   T   Y   V   R   C   L 50                  60                  70                  80
AAT GTT GGA CTA ATT AGG AAG CTG TCA GAT TTT ATT GAT CCT
 N   V   G   L   I   R   K   L   S   D   F   I   D   P 90                 100                 110                 120
CAA GAA GGA TGG AAG AAG TTA GCT GTA GCT ATT AAA AAA CCA
 Q   E   G   W   K   K   L   A   V   A   I   K   K   P 130                 140                 150                 160
TCT GGT GAT GAT AGA TAC AAT CAG TTT CAC ATA AGG AGA TTT
 S   G   D   D   R   Y   N   Q   F   H   I   R   R   F 170                 180                 190                 200                 210
GAA GCA TTA CTT CAA ACT GGA AAA AGT CCC ACT TCT GAA TTA
 E   A   L   L   Q   T   G   K   S   P   T   S   E   L 220                 230                 240                 250
CTG TTT GAC TGG GGC ACC ACA AAT TGC ACA GCT GGT GAT CTT
 L   F   D   W   G   T   T   N   C   T   A   G   D   L 260                 270                 280                 290
GTG GAT CTT TTG ATC CAA AAT GAA TTT TTT GCT CCT GCG AGT
 V   D   L   L   I   Q   N   E   F   F   A   P   A   S 300                 310                 320                 330
CTT TTG CTC CCA GAT GCT GTT CCC AAA ACT GCT AAT ACA CTA
 L   L   L   P   D   A   V   P   K   T   A   N   T   L 340                 350                 360                 370
CCT TCT AAA GAA GCT ATA ACA GTT CAG CAA AAA CAG ATG CCT
 P   S   K   E   A   I   T   V   Q   Q   K   Q   M   P 380                 390                 400                 410                 420
TTC TGT GAC AAA GAC AGG ACA TTG ATG ACA CCT GTG CAG AAT
 F   C   D   K   D   R   T   L   M   T   P   V   Q   N
```

FIG. 2A.

```
                430             440             450             460
CTT GAA CAA AGC TAT ATG CCA CCT GAC TCC TCA AGT CCA GAA
 L   E   Q   S   Y   M   P   P   D   S   S   S   P   E 470             480             490             500
AAT AAA AGT TTA GAA GTT AGT GAT ACA CGT TTT CAC AGT TTT
 N   K   S   L   E   V   S   D   T   R   F   H   S   F 510             520             530             540
TCA TTT TAT GAA TTG AAG AAT GTC ACA AAT AAC TTT GAT GAA
 S   F   Y   E   L   K   N   V   T   N   N   F   D   E 550             560             570             580
CGA CCC ATT TCT GTT GGT GGT AAT AAA ATG GGA GAG GGA GGA
 R   P   I   S   V   G   G   N   K   M   G   E   G   G 590             600             610             620             630
TTT GGA GTT GTA TAT AAA GGC TAC GTA AAT AAC ACA ACT GTG
 F   G   V   V   Y   K   G   Y   V   N   N   T   T   V 640             650             660             670
GCA GTG AAG AAG CTT GCA GCA ATG GTT GAC ATT ACT ACT GAA
 A   V   K   K   L   A   A   M   V   D   I   T   T   E 680             690             700             710
GAA CTG AAA CAG CAG TTT GAT CAA GAA ATA AAA GTA ATG GCA
 E   L   K   Q   Q   F   D   Q   E   I   K   V   M   A 720             730             740             750
AAG TGT CAA CAT GAA AAC TTA GTA GAA CTA CTT GGT TTC TCA
 K   C   Q   H   E   N   L   V   E   L   L   G   F   S 760             770             780             790
AGT GAT GGA GAT GAC CTC TGC TTA GTA TAT GTT TAC ATG CCT
 S   D   G   D   D   L   C   L   V   Y   V   Y   M   P 800             810             820             830             840
AAT GGT TCA TTG CTA GAC AGA CTC TCT TGC TTG GAT GGT ACT
 N   G   S   L   L   D   R   L   S   C   L   D   G   T
```

*FIG. 2B.*

```
              850            860           870           880
CCA CCA CTT TCT TGG CAC ATG AGA TGC AAG ATT GCT CAG GGT
 P   P   L   S   W   H   M   R   C   K   I   A   Q   G 890           900           910           920
GCA GCT AAT GGC ATC AAT TTT CTA CAT GAA AAT CAT CAT ATT
 A   A   N   G   I   N   F   L   H   E   N   H   H   I 930           940           950           960
CAT AGA GAT ATT AAA AGT GCA AAT ATC TTA CTG GAT GAA GCT
 H   R   D   I   K   S   A   N   I   L   L   D   E   A 970           980           990          1000
TTT ACT GCT AAA ATA TCT GAC TTT GGC CTT GCA CGG GCT TCT
 F   T   A   K   I   S   D   F   G   L   A   R   A   S 1010          1020          1030          1040          1050
GAG AAG TTT GCC CAG ACA GTC ATG ACT AGC AGA ATT GTG GGA
 E   K   F   A   Q   T   V   M   T   S   R   I   V   G 1060          1070          1080          1090
ACA ACA GCT TAT ATG GCA CCA GAA GCT TTG CGT GGA GAA ATA
 T   T   A   Y   M   A   P   E   A   L   R   G   E   I 1100          1110          1120          1130
ACA CCC AAA TCT GAT ATT TAC AGC TTT GGT GTG GTT TTA CTA
 T   P   K   S   D   I   Y   S   F   G   V   V   L   L 1140          1150          1160          1170
GAA ATA ATA ACT GGA CTT CCA GCT GTG GAT GAA CAC CGT GAA
 E   I   I   T   G   L   P   A   V   D   E   H   R   E 1180          1190          1200          1210
CCT CAG TTA TTG CTA GAT ATT AAA GAA GAA ATT GAA GAT GAA
 P   Q   L   L   L   D   I   K   E   E   I   E   D   E 1220          1230          1240          1250          1260
GAA AAG ACA ATT GAA GAT TAT ATT GAT AAA AAG ATG AAT GAT
 E   K   T   I   E   D   Y   I   D   K   K   M   N   D
```

FIG. 2C.

```
         1270            1280             1290            1300
GCT GAT TCC ACT TCA GTT GAA GCT ATG TAC TCT GTT GCT AGT
 A   D   S   T   S   V   E   A   M   Y   S   V   A   S 1310            1320             1330            1340
CAA TGT CTG CAT GAA AAG AAA AAT AAG AGA CCA GAC ATT AAG
 Q   C   L   H   E   K   K   N   K   R   P   D   I   K 1350            1360             1370            1380
AAG GTT CAA CAG CTG CTG CAA GAG ATG ACA GCT TCT TAA
 K   V   Q   Q   L   L   Q   E   M   T   A   S   *>
```

FIG. 2D.

```
         10          20          30          40
MNK PLT PST YIR NLN VGI LRK LSD FID PQE GWK KLA VAI KKP 50          60          70          80
SGD DRY NQF HIR RFE ALL QTG KSP TCE LLF DWG TTN CTV GDL 90         100         110         120
VDL LVQ IEL FAP ATL LLP DAV PQT VKS LPP REA ATV AQT HGP 130         140         150         160
CQE KDR TSV MPM PKL EHS CEP PDS SSP DNR SVE SSD TRF HSF 170         180         190         200         210
SFH ELK SIT NNF DEQ PAS AGG NRM GEG GFG VVY KGC VNN TIV 220         230         240         250
AVK KLG AMV KIS TEE LKQ QFD QEI KVM ATC QHE NLV ELL GFS 260         270         280         290
SDG DNL CLV YAY MPN GSL LDR LSC LDG TPP LSW HTR CKV AQG 300         310         320         330
TAN GIR FLH ENH HIH RDI KSA NIL LDK DFT AKI SDF GLA RAS 340         350         360         370
ARL AQT VMT SRI VGT TAY MAP EAL RGE ITP KSD IYS FGV VLL 380         390         400         410         420
ELI TGL AAV DEN REP QLL LDI KEE IED EEK TIE DYT DEK MSD 430         440         450         460
ADP ASV EAM YSA ASQ CLH EKK NRR PDI AKV QQL LQE MSA *
```

FIG. 3.

```
            10              20              30              40
GCG GCC GCG TCG ACA TGC CCC GGT GAC CCG CAG CAT CCC GAT 50              60              70              80
CGC AGG CAG TCT GAA GTC GCC TGG TGG TCC TGC GTC CTC CAC 90             100             110             120
CCC CGA GTC CTC GCC GGA CGT GGC GGG ACG CCG ATC GCC TTG 130             140             150             160
TCC AGG AAG CGA GGG ACG TCC GAG AGG AAG TAG AAG ATG AAC
                                                 M   N 170             180             190             200             210
AAG CCG TTG ACA CCA TCG ACA TAC ATA CGC AAC CTT AAT GTG
 K   P   L   T   P   S   T   Y   I   R   N   L   N   V 220             230             240             250
GGG ATC CTT AGG AAG CTG TCG GAT TTT ATT GAT CCT CAA GAA
 G   I   L   R   K   L   S   D   F   I   D   P   Q   E 260             270             280             290
GGG TGG AAG AAA TTA GCA GTA GCT ATC AAA AAG CCG TCC GGC
 G   W   K   K   L   A   V   A   I   K   K   P   S   G 300             310             320             330
GAC GAC AGA TAC AAT CAG TTC CAT ATA AGG AGA TTC GAA GCC
 D   D   R   Y   N   Q   F   H   I   R   R   F   E   A 340             350             360             370
TTA CTT CAG ACC GGG AAG AGC CCC ACC TGT GAA CTG CTG TTT
 L   L   Q   T   G   K   S   P   T   C   E   L   L   F 380             390             400             410             420
GAC TGG GGC ACC ACG AAC TGC ACA GTT GGC GAC CTT GTG GAT
 D   W   G   T   T   N   C   T   V   G   D   L   V   D 430             440             450             460
CTA CTG GTC CAG ATT GAG CTG TTT GCC CCC GCC ACT CTC CTG
 L   L   V   Q   I   E   L   F   A   P   A   T   L   L
```

FIG. 4A.

```
       470           480           490            500
CTG CCG GAT GCC GTT CCC CAA ACC GTC AAA AGC CTG CCT CCT
 L   P   D   A   V   P   Q   T   V   K   S   L   P   P 510           520           530           540
AGA GAA GCG GCA ACA GTG GCA CAA ACA CAC GGG CCT TGT CAG
 R   E   A   A   T   V   A   Q   T   H   G   P   C   Q 550           560           570           580
GAA AAG GAC AGG ACA TCC GTA ATG CCT ATG CCG AAG CTA GAA
 E   K   D   R   T   S   V   M   P   M   P   K   L   E 590           600           610           620            630
CAC AGC TGC GAG CCA CCG GAC TCC TCA AGC CCA GAC AAC AGA
 H   S   C   E   P   P   D   S   S   S   P   D   N   R 640           650           660           670
AGT GTA GAG TCC AGC GAC ACT CGG TTC CAC AGC TTC TCG TTC
 S   V   E   S   S   D   T   R   F   H   S   F   S   F 680           690           700           710
CAT GAA CTG AAG AGC ATC ACA AAC AAC TTC GAC GAG CAA CCC
 H   E   L   K   S   I   T   N   N   F   D   E   Q   P 720           730           740           750
GCG TCT GCC GGT GGC AAC CGG ATG GGA GAG GGG GGA TTT GGA
 A   S   A   G   G   N   R   M   G   E   G   G   F   G 760           770           780           790
GTG GTG TAC AAG GGC TGT GTG AAC AAC ACC ATC GTG GCG GTG
 V   V   Y   K   G   C   V   N   N   T   I   V   A   V 800           810           820           830            840
AAG AAG CTC GGA GCG ATG GTT GAA ATC AGT ACT GAA GAA CTA
 K   K   L   G   A   M   V   E   I   S   T   E   E   L 850           860           870           880
AAG CAA CAG TTT GAT CAA GAA ATT AAA GTA ATG GCA ACG TGT
 K   Q   Q   F   D   Q   E   I   K   V   M   A   T   C
```

*FIG. 4B.*

```
      890             900             910             920
CAG CAC GAG AAC CTG GTG GAG CTG CTC GGC TTC TCC AGC GAC
 Q   H   E   N   L   V   E   L   L   G   F   S   S   D 930             940             950             960
AGC GAC AAC CTG TGC TTA GTG TAT GCT TAC ATG CCC AAC GGG
 S   D   N   L   C   L   V   Y   A   Y   M   P   N   G 970             980             990            1000
TCC TTG CTG GAC AGA CTG TCC TGC CTG GAT GGT ACA CCA CCG
 S   L   L   D   R   L   S   C   L   D   G   T   P   P 1010         1020            1030            1040            1050
CTT TCC TGG CAC ACA AGG TGC AAG GTT GCT CAG GGG ACA GCA
 L   S   W   H   T   R   C   K   V   A   Q   G   T   A 1060            1070            1080            1090
AAT GGC ATC AGG TTT CTG CAT GAA AAT CAT CAC ATT CAT AGA
 N   G   I   R   F   L   H   E   N   H   H   I   H   R 1100            1110            1120            1130
GAT ATT AAA AGT GCA AAT ATC TTA CTA GAC AAA GAC TTT ACT
 D   I   K   S   A   N   I   L   L   D   K   D   F   T 1140            1150            1160            1170
GCC AAA ATA TCT GAC TTT GGG CTT GCA CGG GCT TCG GCA AGG
 A   K   I   S   D   F   G   L   A   R   A   S   A   R 1180            1190            1200            1210
CTA GCG CAG ACG GTC ATG ACC AGC CGA ATC GTG GGC ACA ACG
 L   A   Q   T   V   M   T   S   R   I   V   G   T   T 1220            1230            1240            1250            1260
GCT TAC ATG GCA CCC GAA GCT TTG CGG GGA GAA ATA ACA CCC
 A   Y   M   A   P   E   A   L   R   G   E   I   T   P 1270            1280            1290            1300
AAA TCT GAC ATC TAC AGC TTC GGC GTG GTT CTG TTG GAG CTG
 K   S   D   I   Y   S   F   G   V   V   L   L   E   L
```

FIG. 4C.

```
          1310                1320                1330                1340
ATA ACC GGG CTG GCG GCT GTG GAT GAA AAC CGT GAA CCT CAA
 I   T   G   L   A   A   V   D   E   N   R   E   P   Q 1350                1360                1370                1380
CTA CTG CTG GAT ATT AAA GAA GAG ATT GAA GAT GAA GAG AAG
 L   L   L   D   I   K   E   E   I   E   D   E   E   K 1390                1400                1410                1420
ACG ATT GAA GAT TAC ACG GAT GAG AAG ATG AGC GAT GCG GAC
 T   I   E   D   Y   T   D   E   K   M   S   D   A   D 1430                1440                1450                1460           1470
CCT GCT TCG GTG GAA GCA ATG TAC TCT GCT GCT AGC CAG TGT
 P   A   S   V   E   A   M   Y   S   A   A   S   Q   C 1480                1490                1500                1510
CTG CAT GAG AAG AAA AAC AGA CGG CCA GAC ATT GCA AAG GTT
 L   H   E   K   K   N   R   R   P   D   I   A   K   V 1520                1530                1540
CAA CAG CTG CTA CAA GAG ATG TCT GCT TAA
 Q   Q   L   L   Q   E   M   S   A   *>
```

FIG. 4D.

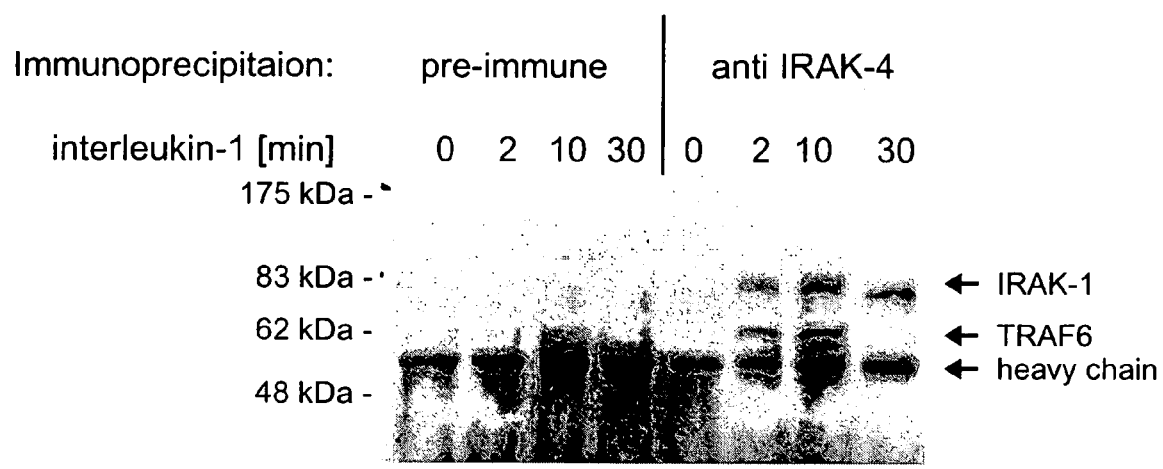
FIG. 5.

IRAK-4: COMPOSITIONS AND METHODS OF USE

CROSS-REFERENCE TO RELATED APPLICATION

This application claims the benefit of U.S. Provisional Patent Application Ser. No. 60/176,395, filed Jan. 13, 2000, which is incorporated herein by reference in its entirety for all purposes.

BACKGROUND OF THE INVENTION

The proinflammatory cytokine interleukin-1 (IL-1) functions in the generation of systemic and local responses to infection, injury and immunological challenges. The importance of IL-1 in inflammation has been demonstrated by the ability of the highly specific IL-1 receptor antagonist protein (IL-1Ra, or IRAP) to relieve inflammatory conditions (for review, see, e.g., Dinarello, *Cytokine Growth Factor Rev.* 8:253–265 (1997)). IL-1 is produced primarily by activated macrophages and monocytes, and is involved in lymphocyte activation, fever, leukocyte trafficking, the acute phase response, cartilage remodeling and other processes. IL-1 exerts its effects by binding to a receptor, IL-1RI, located on the plasma membrane of responsive cells. Among the results of IL-1 binding to the IL-1RI receptor is the activation of the NF-κB transcription factor, ultimately leading to the expression of numerous genes involved in inflammation, such as cytokines, growth factors, immunoreceptors, and cell adhesion molecules (for review, see, e.g., Lee, et al., *J. Clin. Pharmacol.* 38(11):981–93 (1998)).

Several proteins have been discovered to mediate signal transduction following IL-1RI activation, ultimately leading to the activation of NF-kB. For example, the IL-1R accessory protein, IL-1RAcP, has been shown to associate with the IL-1RI receptor following binding to IL-1, thereby initiating the signal transduction cascade (Greenfeder, et al., *J. Biol. Chem.* 270(23):13757–65 (1995)). In addition, three IL-1 receptor-associated kinases (IRAKs) have been identified, IRAK ("IRAK-1;" Cao, et al., *Science* 271:1128–1131 (1996)), IRAK-2 (Muzio, et al., *Science* 278:1612–1615 (1997)), and the monomyeloic cell-specific IRAK-M (Wesche, et al., *J. Biol. Chem.* 274:19403–10 (1999)). IRAK has been shown to be phosphorylated and to associate with IL-1RI in an IL-1 dependent manner. In addition, the MyD88 protein has been shown to mediate the association of IRAK proteins to the activated IL-1 receptor (Wesche, et al., 7:837–47 (1997)). Also, TRAF6 transduces the IRAK signal to downstream effector molecules (Cao, et al., *Nature* 383:443–6 (1996)). The IRAK proteins, as well as MyD88, have been shown to play a role in transducing signals other than those originating from IL-1R receptors, including signals triggered by activation of IL-18 receptors (Kanakaraj, et al. *J. Exp. Med.* 189(7):1129–38 (1999)) and LPS receptors (Yang, et al., *J. Immunol.* 163:639–643 (1999); Wesche, et al., *J. Biol. Chem.* 274:19403–10 (1999)). Overexpression of IRAK-2 and IRAK-M has been shown to be capable of reconstituting the response to IL-1 and LPS in an IRAK deficient cell line.

The IL-1 signal transduction cascade is analogous to a signaling cascade in *Drosophila melanogaster* that is involved in the establishment of dorsal ventral polarity during the early development of *Drosophila* embryos. Specifically, in *Drosophila*, the extracellular ligand Spaetzle binds to a receptor called Toll, which shares homology to IL-1R. In addition, a serine/threonine kinase acting downstream of Toll activation, Pelle is homologous to IRAK kinases (Cao, et al., *Science* 271:1128–1131 (1996); Muzio, et al., *Science* 278:1612–1615 (1997); Wesche, et al., *J. Biol. Chem.* 274:403–410 (1999)). Finally, activation of the Toll receptor results in the activation of the transcription factor Dorsal, which is homologous to NF-κB. Dorsal is inhibited in *Drosophila* cells by Cactus, which is itself homologous to the NF-κB inhibitor IκB.

The present invention is based on the identification of a novel member of the IRAK family, IRAK-4. Nucleic acid and protein sequences for IRAK-4 are provided, as are methods of making IRAK-4 nucleic acids and proteins. Also provided are methods of using IRAK-4 polynucleotides and polypeptides, including methods of using the herein-disclosed sequences to isolate compounds useful in the treatment or prevention of any of a number of inflammatory diseases and conditions.

SUMMARY OF THE INVENTION

The present invention provides novel nucleic acids and polypeptides for mammalian IRAK-4, a new member of the IRAK gene family. IRAK kinases associate with activated IL-1, IL-18 and other receptors and act to transduce signals originating from the activated receptors, ultimately leading to a variety of downstream effects such as NF-κB activation.

In one aspect, an isolated nucleic acid is provided encoding an IRAK-4 polypeptide, the polypeptide comprising at least about 98% amino acid sequence identity to SEQ ID NO:1 or to a subsequence thereof, wherein the amino acid sequence of the polypeptide comprises an alanine residue at an amino acid position corresponding to amino acid position 81 of SEQ ID NO:1, and wherein said nucleic acid comprises at least about 400 nucleotides.

In one embodiment, the polypeptide further comprises an amino acid selected from the group consisting of: (i) a valine residue at an amino acid position corresponding to amino acid position 432 of SEQ ID NO:1; (ii) a leucine residue at an amino acid position corresponding to amino acid position 437 of SEQ ID NO:1; (iii) an arginine residue at an amino acid position corresponding to amino acid position 444 of SEQ ID NO:1; and (iv) a glutamine residue at an amino acid position corresponding to amino acid position 451 of SEQ ID NO:1. In another embodiment, the polypeptide comprises each of the amino acids listed as (i) to (iv). In another embodiment, the polypeptide comprises an amino acid sequence of SEQ ID NO:1. In another embodiment, the polypeptide comprises at least about 100 amino acids. In another embodiment, the polypeptide comprises at least about 450 amino acids.

In another embodiment, the nucleic acid comprises a cytosine at a nucleotide position corresponding to nucleotide position 242 of SEQ ID NO:2. In another embodiment, the nucleic acid further comprises a nucleotide selected from the group consisting of: (i) a thymine at a nucleotide position corresponding to nucleotide position 1295 of SEQ ID NO:2; (ii) a thymine at a nucleotide position corresponding to nucleotide position 1302 of SEQ ID NO:2; (iii) a thymine at a nucleotide position corresponding to nucleotide position 1310 of SEQ ID NO:2; (iv) an adenine at a nucleotide position corresponding to nucleotide position 1332 of SEQ ID NO:2; and (v) an adenine at a nucleotide position corresponding to nucleotide position 1353 of SEQ ID NO:2. In another embodiment, the nucleic acid comprises each of the nucleotides listed as (i) to (v). In another embodiment, the nucleic acid comprises a nucleotide sequence of SEQ ID NO:2. In another embodiment, the nucleic acid comprises at least about 350 nucleotides. In another embodiment, the polypeptide specifically binds to antibodies generated against a polypeptide comprising an amino acid sequence of SEQ ID NO:1.

In another aspect, the present invention provides an isolated IRAK-4 polypeptide, the polypeptide having at least about 98% amino acid sequence identity to SEQ ID NO:1 or to a subsequence thereof, wherein the amino acid sequence of the polypeptide comprises an alanine residue at an amino acid position corresponding to amino acid position 81 of SEQ ID NO:1, and wherein the polypeptide comprises at least about 100 amino acids.

In one embodiment, the polypeptide further comprises an amino acid selected from the group consisting of: (i) a valine residue at an amino acid position corresponding to amino acid position 432 of SEQ ID NO:1; (ii) a leucine residue at an amino acid position corresponding to amino acid position 437 of SEQ ID NO:1; (iii) an arginine residue at an amino acid position corresponding to amino acid position 444 of SEQ ID NO:1; and (iv) a glutamine residue at an amino acid position corresponding to amino acid position 451 of SEQ ID NO:1. In another embodiment, the polypeptide comprises all of the amino acids listed as (i) to (iv). In another embodiment, the polypeptide comprises an amino acid sequence of SEQ ID NO:1. In another embodiment, the polypeptide is encoded by a nucleic acid comprising a nucleotide sequence of SEQ ID NO:2. In another embodiment, the polypeptide specifically binds to antibodies generated against a polypeptide comprising an amino acid sequence of SEQ ID NO:1. In another embodiment, the polypeptide comprises at least about 450 amino acids.

In another aspect, the present invention provides an isolated nucleic acid encoding an IRAK-4 polypeptide, the polypeptide comprising at least about 70% amino acid sequence identity to SEQ ID NO:3 or a subsequence thereof.

In one embodiment, the polypeptide comprises an amino acid sequence of SEQ ID NO:3. In another embodiment, the nucleic acid comprises at least about 70% nucleotide sequence identity to SEQ ID NO:4 or to a subsequence thereof. In another embodiment, the nucleic acid comprises a nucleotide sequence of SEQ ID NO:4. In another embodiment, the nucleic acid hybridizes under stringent hybridization conditions to a nucleic acid comprising a nucleotide sequence of SEQ ID NO:4.

In certain embodiments, the above nucleic acids are operably linked to a promoter. In other aspects, the present invention provides expression cassettes comprising the nucleic acids, wherein the nucleic acids are operably linked to a promoter. In other aspects, the present invention provides isolated cells comprising an expression cassette.

In another aspect, the present invention provides a method of making an IRAK-4 polypeptide, the method comprising: (i) introducing a nucleic acid into a host cell or cellular extract, the nucleic acid encoding a polypeptide comprising either: (a) at least about 98% amino acid sequence identity to SEQ ID NO:1 or to a subsequence thereof, wherein the polypeptide comprises an alanine residue at an amino acid position corresponding to amino acid position 81 of SEQ ID NO:1, and wherein the nucleic acid comprises at least about 400 nucleotides; or (b) at least about 70% amino acid sequence identity to SEQ ID NO:3 or to a subsequence thereof; (ii) incubating said host cell or cellular extract under conditions such that the IRAK-4 polypeptide is expressed in the host cell or cellular extract; and (ii) recovering the IRAK-4 polypeptide from the host cell or cellular extract.

In another aspect, the present invention provides a method of identifying a compound useful in the treatment of inflammatory diseases, the method comprising the steps of: (i) contacting an IRAK-4 polypeptide with the compound, wherein the IRAK-4 polypeptide comprises at least about 70% amino acid sequence identity to SEQ ID NO:1 or SEQ ID NO:3; and (ii) determining the functional effect of the compound on the IRAK-4 polypeptide.

In one embodiment, the IRAK-4 polypeptide comprises an amino acid sequence shown as SEQ ID NO:1 or SEQ ID NO:3. In another embodiment, the compound inhibits IRAK-4 kinase activity. In another embodiment, the IRAK-4 is present inside of a eukaryotic cell.

In another aspect, the present invention provides a method of treating an inflammatory disease in a patient, the method comprising administering to the patient a therapeutically effective amount of a compound identified using the method comprising the steps of: (i) contacting an IRAK-4 polypeptide with the compound, wherein the IRAK-4 polypeptide comprises at least about 70% amino acid sequence identity to SEQ ID NO:1 or SEQ ID NO:3; and (ii) determining the functional effect of the compound on the IRAK-4 polypeptide.

In one embodiment, the inflammatory disease is selected from the group consisting of pulmonary diseases and diseases of the airway, transplant rejection, autoimmune diseases, cancer, cardiovascular diseases, diseases of the central nervous system, CD14 mediated sepsis, non-CD14 mediated sepsis, osteoarthritis, osteoporosis, psoriasis, diseases of the skin, inflammatory bowel disease, Behcet's syndrome, ankylosing spondylitis, sarcoidosis, gout, and ophthalmic diseases and conditions.

In one embodiment, the pulmonary disease and disease of the airway is selected from the group consisting of Adult Respiratory Disease Syndrome (ARDS), Chronic Obstructive Pulmonary Disease (OPD), pulmonary fibrosis, interstitial lung disease, asthma, chronic cough, and allergic rhinitis. In another embodiment, the autoimmune disease is selected from the group consisting of rheumatoid arthritis, systemic lupus erythematosus, multiple sclerosis, and diabetes (e.g., type 1 diabetes mellitus). In another embodiment, the cancer is selected from the group consisting of solid tumors, skin cancer, and lymphoma. In another embodiment, the cardiovascular disease is selected from the group consisting of stroke and atherosclerosis. In another embodiment, the disease of the central nervous system is a neurodegenerative disease. In another embodiment, the disease of the skin is selected from the group consisting of rash, contact dermatitis, and atopic dermatitis. In another embodiment, the inflammatory bowel disease is selected from the group consisting of Crohn's disease and ulcerative colitis.

In another aspect, the present invention provides a method of inhibiting the transduction of a signal resulting from the activation of an IL-1R/Toll receptor in a cell, the method comprising introducing into the cell an inhibitor of the activity or expression of IRAK-4.

In one embodiment, the IL-1R/Toll receptor is activated by IL-1. In another embodiment, the inhibitor comprises a dominant negative form of IRAK-4. In another embodiment, the dominant negative form of IRAK-4 comprises a mutation in a lysine residue in the ATP binding pocket. In another embodiment, the mutation comprises a substitution of alanine residues for lysine residues within the IRAK-4 at amino acid positions corresponding to positions 213 and 214 of SEQ ID NO:1. In another embodiment, the dominant negative form of IRAK-4 is a truncated form of IRAK-4. In another embodiment, the truncated form of IRAK-4 consists essentially of amino acids 1 to 191 of SEQ ID NO:1. In another embodiment, the inhibitor comprises a compound identified using the method comprising the steps of: (i) contacting an IRAK-4 polypeptide with the compound, wherein the IRAK-4 polypeptide comprises at least about 70% amino acid sequence identity to SEQ ID NO:1 or SEQ ID NO:3; and (ii) determining the functional effect of the compound on the IRAK-4 polypeptide. In one embodiment, the inhibitor inhibits activation of at least one transcription factor. In another embodiment, the transcription factor activates NFκB in the cell.

In another aspect, the present invention provides a transgenic nonhuman animal that comprises a mutation in an endogenous IRAK-4 gene. In one embodiment, the mutation inactivates the endogenous IRAK-4 gene. In another embodiment, the mutation deletes all or part of the IRAK-4 gene. In another embodiment, the animal is a mouse.

In another aspect, the present invention provides an isolated mammalian cell comprising a mutation in an endogenous IRAK-4 gene. In one embodiment, the mutation inactivates the IRAK-4 gene. In another embodiment, the mutation deletes all or part of the IRAK-4 gene.

DESCRIPTION OF THE DRAWINGS

FIG. 1 provides amino acid sequence for human IRAK-4 (SEQ ID NO:1).

FIG. 2 provides nucleotide sequence for the human IRAK-4 cDNA (SEQ ID NO:2).

FIG. 3 provides amino acid sequence for murine IRAK-4 (SEQ ID NO:3).

FIG. 4 provides nucleotide sequence for the murine IRAK-4 cDNA (SEQ ID NO:4).

FIG. 5 provides data showing that endogenous IRAK-4 physically interacts with both TRAF-6 and IRAK-1 in an IL-1 dependent manner.

DESCRIPTION OF THE SPECIFIC EMBODIMENTS

I. Introduction

The present invention provides nucleic acids and polypeptides for IRAK-4, a novel member of the IRAK family of protein kinases. Members of the IRAK family are indispensable signal transducers for members of the IL-1R/Toll family of transmembrane receptors, including IL-1 receptors, IL-18 receptors and LPS receptors. Like the other IRAK family members, IRAK-4 is able to interact with the adapter proteins MyD88, which links the kinases to the receptor complex (Wesche et al., *Immunity* 7:837–47 (1997)), and to TRAF6, which transduces the signal to downstream effector molecules (Cao et al., *Nature* 383:443–6 (1996)). IRAK-4 sequences from human (see, e.g., SEQ ID NOs: 1 and 2) and mouse (see, e.g., SEQ ID NOs: 3 and 4) are provided.

Modulators, recombinant forms, or fragments of IRAK-4 can be used to interfere with the IL-1/Toll receptor family proinflammatory signaling cascade, and can therefore be useful for the treatment of a large number of inflammatory diseases, including, but not limited to, (a) pulmonary diseases and diseases of the airway, such Adult Respiratory Disease Syndrome (ARDS), Chronic Obstructive Pulmonary Disease (OPD), pulmonary fibrosis, interstitial lung disease, asthma, chronic cough, and allergic rhinitis; b) transplantation; c) the autoimmune diseases such as rheumatoid arthritis, systemic lupus erythematosus, multiple sclerosis, and diabetes (e.g., type 1 diabetes mellitus); d) cancer including solid tumors, skin cancer, and lymphoma; e) cardiovascular diseases including stroke and atherosclerosis; f) diseases of the central nervous system including neurodegenerative diseaeses; g) non-CD14 mediated sepsis; h) osteoarthritis; i) osteoporosis; j) psoriasis and diseases of the skin such as rash and contact and atopic dermatitis; k) inflammatory bowel disease such as Crohn's disease and ulcerative colitis; l) Behcet's syndrome; m) ankylosing spondylitis; n) sarcoidosis; o) gout; p) ophthalmic diseases and conditions; and h) CD14 mediated sepsis.

In numerous embodiments, the present invention provides methods of screening for modulators, e.g., activators, inhibitors, stimulators, enhancers, etc., of IRAK-4 nucleic acids and proteins. Such modulators can affect IRAK-4 activity in any of a number of ways, e.g., by modulating IRAK-4 transcription, translation, phosphorylation, mRNA or protein stability, by altering the binding of IRAK-4 to heterologous proteins or other molecules; or by affecting IRAK-4 protein activity. In preferred embodiments, modulators that inhibit IRAK-4 activity or levels are used to treat any of the above-recited inflammatory diseases.

In one embodiment, compounds are screened, e.g., using high throughput screening (HTS), to identify those compounds that can bind to and/or modulate the activity of an isolated IRAK-4 polypeptide or fragment thereof. In another embodiment, IRAK-4 proteins are recombinantly expressed in cells, and potential modulators of IRAK-4 are assayed by measuring an indicator of IRAK-4 activity, such as NF-κB activity.

In numerous embodiments, an IRAK-4 polynucleotide or polypeptide is introduced into a cell, in vivo or ex vivo, and the IRAK-4 activity in the cell is thereby modulated. For example, a polynucleotide encoding a full length IRAK-4 polypeptide is introduced into a population of cells, thereby increasing the level or activity of IRAK-4 in the cells. Alternatively, an antisense, ribozyme, or dominant-negative encoding polynucleotide can be introduced into a population of cells, thereby inhibiting the IRAK-4, and associated transduction of inflammatory signals, in the cells.

The present invention also provides methods for detecting IRAK-4 nucleic acid and protein expression, allowing investigation into IL-1, IL-18, LPS, and other types of signal transduction, and allowing the specific identification of IL-1, IL-18, or LPS responsive cells. IRAK-4 also provides useful nucleic acid probes for paternity and forensic investigations. IRAK-4 polypeptides can also be used to generate monoclonal and polyclonal antibodies useful for identifying IL-1, IL-18, or LPS responsive cells. IRAK-4 expression can be identified using techniques such as reverse transcription and amplification of mRNA, isolation of total RNA or poly $A^+$ RNA, northern blotting, dot blotting, in situ hybridization, RNase protection, S1 digestion, probing DNA microchip arrays, western blots, and the like.

Functionally, IRAK-4 nucleic acids encode protein kinases that act in the transduction of signals from the IL-1R/Toll family of transmembrane receptors, including IL-1 receptors, IL-18 receptors, and LPS receptors. Structurally, the nucleotide sequence of IRAK-4 (see, e.g., SEQ ID NOs:2 or 4, isolated from humans and mice, respectively) encodes polypeptides comprising an amino-terminal (N-terminal) "death" domain (DD) and a central kinase domain. Related IRAK-4 genes from other species share at least about 60% nucleotide sequence identity over a region of at least about 50 nucleotides in length, optionally 100, 200, 500, or more nucleotides in length, to SEQ ID NO:2 or 4, or encode polypeptides sharing at least about 60% amino acid sequence identity over an amino acid region at least about 25 amino acids in length, optionally 50 to 100 amino acids in length to SEQ ID NO:1 or 3. Preferably, the IRAK-4 polypeptide comprises about 459 or 460 amino acids and has a calculated molecular mass of about 51 or 52 kDa.

The present invention also provides polymorphic variants of the IRAK-4 protein depicted in SEQ ID NO:1: variant #1, in which a leucine residue is substituted for an isoleucine residue at amino acid position 53; and variant #2, in which an alanine residue is substituted for a glycine residue at amino acid position 17.

The present invention also provides polymorphic variants of the IRAK-4 protein depicted in SEQ ID NO:3: variant #1, in which a lysine residue is substituted for an arginine residue at amino acid position 12; and variant #2, in which a valine residue is substituted for a leucine residue at amino acid position 59.

Specific regions of the IRAK-4 nucleotide and amino acid sequences may be used to identify polymorphic variants, interspecies homologs, and alleles of IRAK-4 genes. This identification can be made in vitro, e.g., under stringent hybridization conditions, or PCR and sequencing, or by using the sequence information in a computer system for comparison with other nucleotide sequences. Typically, identification of polymorphic variants and alleles of IRAK-4 is made by comparing an amino acid sequence of about 25 amino acids or more, e.g., 50–100 amino acids. Amino acid identity of approximately at least 60% or above, optionally 65%, 70%, 75%, 80%, 85%, or 90–95% or above typically demonstrates that a protein is a polymorphic variant, interspecies homolog, or allele of IRAK-4. Sequence comparison can be performed using any of the sequence comparison algorithms discussed below. Antibodies that bind specifically to IRAK-4 polypeptides or a conserved region thereof can also be used to identify alleles, interspecies homologs, and polymorphic variants.

Polymorphic variants, interspecies homologs, and alleles of IRAK-4 are confirmed by examining, e.g., the IL-1/Toll receptor association, the NF-kB activating ability, or the MyD88 associating activity, of the putative IRAK-4 polypeptide. Typically, an IRAK-4 polypeptide having an amino acid sequence of SEQ ID NO:1 or SEQ ID NO:3 is used as a positive control in comparison to the putative IRAK-4 protein to demonstrate the identification of a polymorphic variant or allele of the IRAK-4 gene or protein.

Nucleotide and amino acid sequence information for IRAK-4 may also be used to construct models of IRAK-4 polypeptides in a computer system. These models are subsequently used to identify compounds that can activate or inhibit IRAK-4 proteins. Such compounds that modulate the activity of IRAK-4 genes or proteins can be used to investigate the role of IRAK-4 genes in IL-1/Toll signal transduction.

The present invention also provides assays, preferably high throughput assays, to identify compounds or other molecules that interact with and/or modulate IRAK-4. In certain assays, a particular domain of IRAK-4 is used, e.g., an N-terminal or central kinase domain.

The present invention also provides methods to treat diseases or conditions associated with IL-1/Toll receptor activity, such as inflammatory diseases. For example, IRAK-4 activity and/or expression can be altered in cells of a patient with an inflammatory disease including, but not limited to, the following: (a) pulmonary diseases and diseases of the airway including, but not limited to, Adult Respiratory Disease Syndrome (ARDS), Chronic Obstructive Pulmonary Disease (OPD), pulmonary fibrosis, interstitial lung disease, asthma, chronic cough, and allergic rhinitis; b) transplantation; c) the autoimmune diseases including, but not limited to, rheumatoid arthritis, systemic lupus erythematosus, multiple sclerosis, and diabetes (e.g., type 1 diabetes mellitus); d) cancer including, but not limited to, solid tumors, skin cancer and lymphoma; e) cardiovascular diseases including, but not limited to, stroke and atherosclerosis; f) diseases of the central nervous system including, but not limited to, neurodegenerative diseases; g) non-CD14 mediated sepsis; h) osteoarthritis; i) osteoporosis; j) psoriasis and diseases of the skin including, but not limited to, rash and contact and atopic dermatitis; k) inflammatory bowel disease (including, but not limited to, Crohn's disease and ulcerative colitis); l) Behcet's syndrome; m) ankylosing spondylitis; n) sarcoidosis; o) gout; p) ophthalmic diseases and conditions; and q) CD14 mediated sepsis. In such patients, the inhibition of IRAK-4 in, e.g., IL-1 responsive cells will block the transduction of the IL-1 initiated signal, thereby preventing NF-κB activation and thus providing a treatment for the disorder.

Transgenic animals and cells lacking one or more IRAK-4 alleles, or containing altered forms of IRAK-4 are also provided, as are kits for using the herein-disclosed polynucleotides and polypeptides and for practicing the herein-disclosed methods, are also provided.

II. Definitions

As used herein, the following terms have the meanings ascribed to them below unless specified otherwise.

As used herein, "IRAK-4" refers to a protein kinase as shown in SEQ ID NO:1 or 3, or any derivative, homolog, or fragment thereof, or to any nucleic acid encoding such a protein, derivative, homolog, or fragment thereof. IRAK-4 proteins or derivatives can be expressed in any cell type, including any eukaryotic or prokaryotic cell, or synthesized in vitro. Typically, IRAK-4 nucleic acids encode active serine/threonine kinases that bind to TRAF6 and IRAK-1 in a ligand (e.g., IL-1) dependent fashion. It will be recognized that derivatives, homologs, and fragments of IRAK-4 can readily be used in the present invention. Such IRAK-4 variants can comprise any one or more domains of the polypeptide shown as SEQ ID NO:1 or 3, or multiple copies of any one or more domains, or any number of domains in novel combinations with each other or with other proteins or protein domains.

In certain embodiments, an IRAK-4 polypeptide will be at least about 98% identical to SEQ ID NO:1, and will preferably have an alanine residue at an amino acid position corresponding to position 81 of SEQ ID NO:1. Preferably, the IRAK-4 polypeptide will also have at least one of the following amino acids: (i) a valine at an amino acid position corresponding to position 432 of SEQ ID NO:1; (ii) a leucine at an amino acid position corresponding to position 437 of SEQ ID NO:1; (iii) an arginine at an amino acid position corresponding to position 444 of SEQ ID NO:1; or (iv) a glutamine at an amino acid position corresponding to amino acid position 451 of SEQ ID NO:1. Such polypeptides are preferably encoded by a polynucleotide having at least one of the following nucleotides: (i) a cytosine at a nucleotide position corresponding to position 242 of SEQ ID NO:2; (ii) a thymine at a nucleotide position corresponding to nucleotide position 1302 of SEQ ID NO:2; (iii) a thymine at a nucleotide position corresponding to nucleotide position 1310 of SEQ ID NO:2; (iv) an adenine at a nucleotide position corresponding to nucleotide position 1332 of SEQ ID NO:2; or (v) an adenine at a nucleotide position corresponding to nucleotide position 1353 of SEQ ID NO:2.

The term "IRAK-4" also refers to polymorphic variants, alleles, mutants, and interspecies homologs that: (1) have about 60% amino acid sequence identity, optionally about 75, 80, 85, 90, or 95% amino acid sequence identity to SEQ ID NO:1 or 3 over a window of about 25 amino acids, optionally 50–100 amino acids; (2) specifically bind to antibodies raised against an immunogen comprising an amino acid sequence of SEQ ID NO:1 or 3, and conservatively modified variants thereof; or (3) specifically hybridize (with a size of at least about 100, optionally at least about 500–1000 nucleotides) under stringent hybridization conditions to a sequence of SEQ ID NO:2 or 4, and conservatively modified variants thereof.

Topologically, full-length IRAK-4 polypeptides include an "N-terminal domain," or "death domain," and a "central kinase domain." These domains can be structurally identified using methods known to those of skill in the art, such as standard sequence analysis programs and by comparison with related proteins. In addition, like other IRAK proteins, IRAK-4 contains each of the 12 standard subdomains of protein kinases (see, e.g., Cao, et al., *Science* 271:1128–1131 (1996)). The "ATP binding pocket" refers to a conserved kinase domain corresponding, e.g., to subdomain II of the IRAK-1 sequence (see, Cao, et al. (1996)), and which encompasses the lysine residue at position 213 of SEQ ID NO:1 and SEQ ID NO:3.

The "N-terminal domain" or "death domain" refers to a region found in the N-terminus that is homologous to a region of the *Drosophila melanogaster* Pelle protein. In IRAK-4, the "death domain" extends approximately from amino acid 5 to amino acid 147, e.g., as shown in SEQ ID NO:1 or 3 (see, e.g., Feinstein, et al., *Trends Biochem. Sci.* 20:342–4 (1995)).

The "central kinase domain" refers to a conserved region of the IRAK-4 protein that is homologous to other serine/threonine kinases. In IRAK-4, the "central kinase domain" extends approximately from amino acid 192 to amino acid 460 of SEQ ID NO:1 and 3 (see, e.g., Wesche, et al., *J. Biol. Chem.* 274:19403–10 (1999)).

"Biological sample," as used herein, refers to a sample of biological tissue or fluid that contains one or more IRAK-4 nucleic acids encoding one or more IRAK-4 proteins. Such samples include, but are not limited to, tissue isolated from humans and mice, in particular, thymus, spleen, kidney, placenta, lung, liver, kidney, pancreas, prostate, testis, ovary, small intestine, colon, lymph node, and tonsils. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as a chimpanzee or a human.

By "determining the functional effect" is meant assaying for a compound that modulates, e.g., increases or decreases, a parameter that is indirectly or directly under the influence of an IRAK-4 polypeptide, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, changes in gene expression of IRAK-4 or of any marker genes indicative of IRAK-4 activity, and the like.

"Inhibitors," "activators," and "modulators" of IRAK-4 genes or proteins are used interchangeably to refer to inhibitory, activating, or modulating molecules identified using in vitro and in vivo assays for IRAK-4. Inhibitors are compounds that, e.g., bind to IRAK-4 proteins, partially or totally block IRAK-4 activity, down-regulate IRAK-4 expression or stability, or prevent IRAK-4 binding to heterologous molecules, e.g., MyD88, IL-1RI, or TRAF6. Activators are compounds that, e.g., bind to IRAK-4, stimulate IRAK-4 activity, increase IRAK-4 expression or stability, or facilitate IRAK-4 binding to membranes or to any other protein or factor. Modulators may include genetically modified versions of IRAK-4 proteins, e.g., dominant negative or activated forms of IRAK-4. Such assays for inhibitors and activators are described below and include, e.g., expressing IRAK-4 proteins in cells, applying putative modulator compounds, and then determining the functional effects on IRAK-4 activity. Samples or assays comprising IRAK-4 polypeptides that are treated with a potential activator, inhibitor, or modulator are compared to control samples without the inhibitor, activator, or modulator to examine the effect of the candidate compound. Control samples (untreated with the compound) are assigned a relative IRAK-4 activity value of 100%. Inhibition of an IRAK-4 polypeptide is achieved when the activity value relative to the control is about 80%, optionally 50% or 25–0%. Activation of an IRAK-4 polypeptide is achieved when the activity value relative to the control is 110%, optionally 150%, optionally 200–500%, or 1000–3000% higher.

The terms "isolated," "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated IRAK-4 nucleic acid is separated from open reading frames that flank the IRAK-4 gene and encode proteins other than IRAK-4. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, et al., *J. Biol. Chem.* 260:2605–2608 (1985); Rossolini, et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Albertso, et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel, et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux, et al., *Nuc. Acids Res.* 12:387–395 (1984)).

Another example of algorithm that is suitable for determining percent sequence identity and sequence similarity are the BLAST and BLAST 2.0 algorithms, which are described in Altschul, et al., *Nuc. Acids Res.* 25:3389–3402 (1977) and Altschul, et al., *J. Mol. Biol.* 215:403–410 (1990), respectively. Software for performing BLAST analyses is publicly available through the National Center for Biotechnology Information (http://www.ncbi.nlm.nih-.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor, et al., *Immunology Today* 4:72 (1983); Cole, et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty, et al., *Nature* 348:552–554 (1990); Marks, et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-IRAK-4" antibody is an antibody or antibody fragment that specifically binds a polypeptide encoded by an IRAK-4 gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to an IRAK-4 polypeptide from specific species such as rat, mouse, or human can be selected to obtain only those polyclonal antibodies that are specifically immunoreactive with the IRAK-4 protein and not with other proteins, except for polymorphic variants and alleles of the IRAK-4 protein. This selection may be achieved by subtracting out antibodies that cross-react with IRAK-4 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind" to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

III. Manipulation and Detection of IRAK-4 Nucleic Acids

In numerous embodiments of the present invention, nucleic acids encoding an IRAK-4 polypeptide, including a full-length IRAK-4 protein, or any derivative, variant, homolog, or fragment thereof, will be used. Such nucleic acids are useful for any of a number of applications, including for the production of IRAK-4 protein, for diagnostic assays, for therapeutic applications, for IRAK-4 specific probes, for assays for IRAK-4 binding and/or modulating compounds, to identify and/or isolate IRAK-4 homologs from other species, and other applications.

A. General Recombinant DNA Methods

Numerous applications of the present invention involve the cloning, synthesis, maintenance, mutagenesis, and other manipulations of nucleic acid sequences that can be performed using routine techniques in the field of recombinant genetics. Basic texts disclosing the general methods of use in this invention include Sambrook, et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel, et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter, et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace, et al., *Gene* 16:21–26 (1981).

B. Isolating and Detecting IRAK-4 Nucleotide Sequences

In numerous embodiments of the present invention, IRAK-4 nucleic acids will be isolated and cloned using recombinant methods. Such embodiments are used, e.g., to isolate IRAK-4 polynucleotides for protein expression or during the generation of variants, derivatives, expression cassettes, or other sequences derived from IRAK-4, to monitor IRAK-4 gene expression, for the isolation or detection of IRAK-4 sequences in different species, for diagnostic purposes in a patient, i.e., to detect mutations in IRAK-4, or for genotyping and/or forensic applications.

Often, the nucleic acid sequences encoding IRAK-4 proteins and related nucleic acid sequence homologs are cloned from cDNA and genomic DNA libraries by hybridization with probes, or isolated using amplification techniques with oligonucleotide primers. For example, IRAK-4 sequences are typically isolated from mammalian nucleic acid (genomic or cDNA) libraries by hybridizing with a nucleic acid probe, the sequence of which can be derived from SEQ ID NO:2 or 4, or amplified using primers comprising SEQ ID NOs: 5 and 6. A suitable biological material from which RNA and cDNA for IRAK-4 can be isolated is, e.g., thymus, spleen, kidney, placenta, lung, liver, kidney, pancreas, prostate, testis, ovary, small intestine, colon, lymph node, and tonsils.

Amplification techniques using primers can also be used to amplify and isolate IRAK-4 sequences from DNA or RNA (see, e.g., Dieffenfach & Dveksler, *PCR Primer: A Laboratory Manual* (1995)). Primers can be used, e.g., to amplify either the full length sequence or a probe of from one to several hundred nucleotides (using, e.g., primers shown as SEQ ID NOs: 5 and 6), which is then used to screen a mammalian library for full-length IRAK-4 clones.

Nucleic acids encoding IRAK-4 polypeptides can also be isolated from expression libraries using antibodies as probes. Such polyclonal or monoclonal antibodies can be raised using the sequence of SEQ ID NO:1 or 3, or derivatives or fragments thereof.

Polymorphic variants, alleles, and interspecies homologs that are substantially identical to an IRAK-4 gene can be isolated using IRAK-4 nucleic acid probes, and oligonucleotides under stringent hybridization conditions, by screening libraries. Alternatively, expression libraries can be used to clone IRAK-4 polymorphic variants, alleles, and interspecies homologs, by detecting expressed homologs immunologically with antisera or purified antibodies made against an IRAK-4 polypeptide, which also recognize and selectively bind to the IRAK-4 homolog.

More distantly related IRAK-4 homologs can be identified using any of a number of well known techniques, including by hybridizing a IRAK-4 probe with a genomic or cDNA library using moderately stringent conditions, or under low stringency conditions. Also, a distant homolog can be amplified from a nucleic acid library using degenerate primer sets, i.e., primers that incorporate all possible codons encoding a given amino acid sequence, in particular based on a highly conserved amino acid stretch. Such primers are well known by those of skill, and numerous programs are available, e.g., on the Internet, for degenerate primer design.

To make a cDNA library, one should choose a source that is rich in IRAK-4 mRNA, e.g., cells isolated from thymus, spleen, kidney, placenta, lung, liver, kidney, pancreas, prostate, testis, ovary, small intestine, colon, lymph node, or tonsils. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook, et al., supra; Ausubel, et al., supra).

For a genomic library, the DNA is extracted from the tissue or cells and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating IRAK-4 nucleic acid and its homologs combines the use of synthetic oligonucleotide primers and amplification of an RNA or DNA template (see, U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of IRAK-4 genes directly from mRNA, from cDNA, from genomic libraries or cDNA libraries. Degenerate oligonucleotides can be designed to amplify IRAK-4 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of IRAK-4-encoding mRNA in physiological samples, for nucleic acid sequencing, or for other purposes. Genes amplified by the PCR reaction can be purified from agarose gels and cloned into an appropriate vector.

Synthetic oligonucleotides can be used to construct recombinant IRAK-4 genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the IRAK-4 nucleic acid. The specific subsequence is then ligated into an expression vector.

The nucleic acid encoding an IRAK-4 polypeptide is typically cloned into intermediate vectors before transformation into prokaryotic or eukaryotic cells for replication and/or expression. These intermediate vectors are typically prokaryote vectors, e.g., plasmids, or shuttle vectors. Vectors, cells, and transfection methods are well known to those of skill and are described, e.g., in Ausubel or in Sambrook, both supra.

Optionally, nucleic acids will be used that encode chimeric proteins comprising an IRAK-4 polypeptide or domains thereof in combination with a heterologous polypeptide or polypeptides. For example, a domain such as an N-terminal "death" domain, a central kinase domain, or any of the 12 conserved kinase domains, can be covalently linked to a heterologous protein such as a heterologous transmembrane domain or a heterologous extracellular domain. Other heterologous proteins of choice include, e.g., luciferase, green fluorescent protein (GFP), and β-gal, each of which is well known in the art.

In certain embodiments, IRAK-4 polynucleotides will be detected using hybridization-based methods to determine, e.g., IRAK-4 RNA levels or to detect particular DNA sequences, e.g., for genotyping or for forensic applications. For example, gene expression of IRAK-4 can be analyzed by techniques known in the art, e.g., Northern blotting, reverse transcription and amplification of mRNA, dot blotting, in situ hybridization, RNase protection, probing DNA microchip arrays, and the like. In one embodiment, high density oligonucleotide analysis technology (e.g., GeneChip™) is used to identify homologs and polymorphic variants of IRAK-4, or to monitor levels of IRAK-4 mRNA. In the case where a homolog is linked to a known disease, they can be used with GeneChip™ as a diagnostic tool in detecting the disease in a biological sample, see, e.g., Gunthand, et al., *AIDS Res. Hum. Retroviruses* 14:869–876 (1998); Kozal, et al., *Nat. Med.* 2:753–759 (1996); Matson, et al., *Anal. Biochem.* 224:110–106 (1995); Lockhart, et al., *Nat. Biotechnol.* 14:1675–1680 (1996); Gingeras, et al., *Genome Res.* 8:435–448 (1998); Hacia, et al., *Nucleic Acids Res.* 26:3865–3866 (1998).

In certain applications, a IRAK-4 nucleic acid sequence (e.g., DNA) will be detected, e.g., for diagnostic or forensic applications. For example, a IRAK-4 allele can be detected in a mammal using Southern blot hybridization, i.e., by isolating genomic DNA, performing a restriction digest on the isolated DNA, separating the restriction fragments electrophoretically, e.g., in an agarose gel, and transferring the separated DNA to a membrane and probing with a specific, labeled sequence. Southern blotting is well known to those of skill, and is taught in numerous sources, including Ausubel et al. and Sambrook et al.

In other embodiments, e.g., to detect tissue specific or temporal patterns of gene expression, a IRAK-4 polynucleotide is detected using in situ hybridization. In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase, et al., *Methods in Virology*, vol. VII, pp. 189–226 (1984); and *Nucleic Acid Hybridization: A Practical Approach* (Hames, et al., eds. 1987).

C. Expression in Prokaryotes and Eukaryotes

Often, a cloned IRAK-4 sequence will be expressed in a prokaryotic or eukaryotic cell to obtain expression, i.e., production of the encoded mRNA or protein. For example, in numerous embodiments, a IRAK-4 polynucleotide will be introduced into a cell to modulate the level of IRAK-4 activity in the cell, and thereby to modulate the level of IL-1, IL-18, or LPS signal transduction within cells of a patient. To obtain high level expression of a cloned gene or nucleic acid, such as a cDNA encoding an IRAK-4 polypeptide, a IRAK-4 sequence is typically subcloned into an expression vector that contains a strong promoter to direct transcription, a transcription/translation terminator, and if for a nucleic acid encoding a protein, a ribosome binding site for translational initiation. Suitable bacterial promoters are well known in the art and are described, e.g., in Sambrook, et al. and Ausubel, et al. Bacterial expression systems for expressing the IRAK-4 protein are available in, e.g., *E. coli, Bacillus* sp., and *Salmonella* (Palva, et al., *Gene* 22:229–235 (1983); Mosbach, et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

For therapeutic applications, IRAK-4 nucleic acids are introduced into a cell, in vitro, in vivo, or ex vivo, using any of a large number of methods including, but not limited to, infection with viral vectors, liposome-based methods, biolistic particle acceleration (the gene gun), and naked DNA injection. Such therapeutically useful nucleic acids include, but are not limited to, coding sequences for full-length IRAK-4, coding sequences for an IRAK-4 fragment, domain, derivative, or variant, IRAK-4 antisense sequences, and IRAK-4 ribozymes. Typically, such sequences will be operably linked to a promoter, but in numerous applications a nucleic acid will be administered to a cell that is itself directly therapeutically effective, e.g., certain antisense or ribozyme molecules.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the IRAK-4-encoding nucleic acid in host cells. A typical expression cassette thus contains a promoter operably linked to the nucleic acid sequence encoding an IRAK-4 polypeptide, and signals required for efficient polyadenylation of the transcript, ribosome binding sites, and translation termination. The nucleic acid sequence encoding an IRAK-4 polypeptide may be linked to a cleavable signal peptide sequence to promote secretion of the encoded protein by the transfected cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc, HA-tag, 6-His tag, maltose binding protein, VSV-G tag, anti-DYKDDDDK (SEQ ID NO:7) tag, or any such tag, a large number of which are well known to those of skill in the art.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding an IRAK-4 polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of an IRAK-4 protein, which are then purified using standard techniques (see, e.g., Colley, et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu, et al., eds, 1983).

Any of the well known procedures for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a IRAK-4 gene.

After the expression vector is introduced into the cells, the transfected cells are cultured under conditions favoring expression of the IRAK-4 polypeptide, which is recovered from the culture using standard techniques identified below. Methods of culturing prokaryotic or eukaryotic cells are well known and are taught, e.g., in Ausubel, et al., Sambrook, et al., and in Freshney, *Culture of Animal Cells*, 3d. Ed., (1993), A Wiley-Liss Publication.

IV. Purification of IRAK-4 Polypeptides

Either naturally occurring or recombinant IRAK-4 polypeptides can be purified for use in functional assays, binding assays, diagnostic assays, and other applications. Optionally, recombinant IRAK-4 polypeptides are purified. Naturally occurring IRAK-4 polypeptides are purified, e.g., from mammalian tissue such as thymus, spleen, kidney, placenta, lung, liver, kidney, pancreas, prostate, testis, ovary, small intestine, colon, lymph node, and tonsils, or any other source of an IRAK-4 homolog. Recombinant IRAK-4 polypeptides are purified from any suitable bacterial or eukaryotic expression system, e.g., CHO cells or insect cells.

IRAK-4 proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel, et al., supra; and Sambrook, et al., supra).

A number of procedures can be employed when recombinant IRAK-4 polypeptide is being purified. For example, proteins having established molecular adhesion properties can be reversibly fused to the IRAK-4 polypeptide. With the appropriate ligand, an IRAK-4 polypeptide can be selectively adsorbed to a purification column and then freed from the column in a relatively pure form. The fused protein is then removed by enzymatic activity. IRAK-4 proteins can also be purified using immunoaffinity columns.

A. Purification of IRAK-4 Protein from Recombinant Cells

Recombinant proteins are expressed by transformed bacteria or eukaryotic cells such as CHO cells or insect cells in large amounts, typically after promoter induction; but expression can be constitutive. Promoter induction with IPTG is one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of IRAK-4 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook, et al., supra; Ausubel, et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. IRAK-4 polypeptides are separated from other bacterial proteins by standard separation techniques, e.g., with Ni—NTA agarose resin.

Alternatively, it is possible to purify IRAK-4 polypeptides from bacteria periplasm. After lysis of the bacteria, when an IRAK-4 protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying IRAK-4 Polypeptides

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of an IRAK-4 protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

IRAK-4 proteins can also be separated from other proteins on the basis of its size, net surface charge, hydrophobicity, and affinity for heterologous molecules. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Antibodies to IRAK-4 Family Members

In numerous embodiments of the present invention, antibodies that specifically bind to IRAK-4 polypeptides will be used. Such antibodies have numerous applications, including for the modulation of IRAK-4 activity and for immunoassays to detect IRAK-4, and variants, derivatives, fragments, etc. of IRAK-4. Immunoassays can be used to qualitatively or quantitatively analyze IRAK-4 polypeptides. A general overview of the applicable technology can be found in Harlow & Lane, *Antibodies: A Laboratory Manual* (1988).

Methods of producing polyclonal and monoclonal antibodies that react specifically with IRAK-4 polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse, et al., *Science* 246:1275–1281 (1989); Ward, et al., *Nature* 341:544–546 (1989)).

A number of IRAK-4-comprising immunogens may be used to produce antibodies specifically reactive with an IRAK-4 polypeptide. For example, a recombinant IRAK-4 protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the IRAK-4 polypeptide. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-IRAK-4 proteins, or even related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Using IRAK-4-specific antibodies, individual IRAK-4 proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

A. Immunological Binding Assays

IRAK-4 proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case an IRAK-4 protein or an antigenic subsequence thereof). The antibody (e.g., anti-IRAK-4) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled IRAK-4 polypeptide or a labeled anti-IRAK-4 antibody. Alternatively, the labeling agent may be a third moiety, such a secondary antibody, that specifically binds to the antibody IRAK-4 complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval, et al., *J. Immunol.* 111:1401–1406 (1973); Akerstrom, et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Noncompetitive Assay Formats

Immunoassays for detecting an IRAK-4 protein in a sample may be either competitive or noncompetitive. Noncompetitive immunoassays are assays in which the amount of antigen is directly measured. In one preferred "sandwich" assay, for example, the anti-IRAK-4 antibodies can be bound directly to a solid substrate on which they are immobilized. These immobilized antibodies then capture the IRAK-4 protein present in the test sample. The IRAK-4 protein is thus immobilized is then bound by a labeling agent, such as a second IRAK-4 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

2. Competitive Assay Formats

In competitive assays, the amount of IRAK-4 protein present in the sample is measured indirectly by measuring the amount of a known, added (exogenous) IRAK-4 protein displaced (competed away) from an anti-IRAK-4 antibody by the unknown IRAK-4 protein present in a sample. In one competitive assay, a known amount of IRAK-4 protein is added to a sample and the sample is then contacted with an antibody that specifically binds to the IRAK-4 protein. The amount of exogenous IRAK-4 protein bound to the antibody is inversely proportional to the concentration of IRAK-4 protein present in the sample. In a particularly preferred embodiment, the antibody is immobilized on a solid substrate. The amount of IRAK-4 protein bound to the antibody may be determined either by measuring the amount of IRAK-4 protein present in an IRAK-4/antibody complex, or alternatively by measuring the amount of remaining uncomplexed protein. The amount of IRAK-4 protein may be detected by providing a labeled IRAK-4 molecule.

A hapten inhibition assay is another preferred competitive assay. In this assay the known IRAK-4 protein is immobilized on a solid substrate. A known amount of anti-IRAK-4 antibody is added to the sample, and the sample is then contacted with the immobilized IRAK-4. The amount of anti-IRAK-4 antibody bound to the known immobilized IRAK-4 protein is inversely proportional to the amount of IRAK-4 protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-reactivity Determinations

Immunoassays in the competitive binding format can also be used for crossreactivity determinations. For example, a protein at least partially encoded by SEQ ID NO:2 or 4 can be immobilized to a solid support. Proteins (e.g., IRAK-4 proteins and homologs) are added to the assay that compete for binding of the antisera to the immobilized antigen. The ability of the added proteins to compete for binding of the antisera to the immobilized protein is compared to the ability of the IRAK-4 polypeptide encoded by SEQ ID NO:2 or 4 to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an IRAK-4 protein, to the immunogen protein (i.e., IRAK-4 protein encoded by SEQ ID NO:2 or 4). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 or 4 that is required to inhibit 50% of binding, then the second protein is said to specifically bind to the polyclonal antibodies generated to an IRAK-4 immunogen.

Polyclonal antibodies that specifically bind to an IRAK-4 protein from a particular species can be made by subtracting out cross-reactive antibodies using IRAK-4 homologs. For example, antibodies specific to human IRAK-4 (SEQ ID NO:1) can be made by subtracting out antibodies that are cross-reactive with mouse IRAK-4 (SEQ ID NO:3). In an analogous fashion, antibodies specific to a particular IRAK-4 protein can be obtained in an organism with multiple IRAK-4 genes.

4. Other Assay Formats

Western blot (immunoblot) analysis is used to detect and quantify the presence of IRAK-4 protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the IRAK-4 protein. The anti-IRAK-4 polypeptide antibodies specifically bind to the IRAK-4 polypeptide on the solid support. These antibodies may be directly labeled or alternatively may be subsequently detected using labeled antibodies (e.g., labeled sheep anti-mouse antibodies) that specifically bind to the anti-IRAK-4 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe, et al., *Amer. Clin. Prod. Rev.* 5:34–41 (1986)).

5. Reduction of Nonspecific Binding

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such nonspecific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

6. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Nonradioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize an IRAK-4 protein, or secondary antibodies that recognize anti-IRAK-4.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, e.g., U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Modulating IRAK-4 Activity in Cells

A. Assays for Modulators of IRAK-4 Proteins

In numerous embodiments of this invention, the level of IRAK-4 activity will be modulated in a cell by administering to the cell, in vivo or in vitro, any of a large number of IRAK-4-modulating molecules, e.g., polypeptides, antibodies, amino acids, nucleotides, lipids, carbohydrates, or any organic or inorganic molecule. Such IRAK-4 modulators are particularly useful in the treatment of any of a large number of inflammatory diseases.

To identify molecules capable of modulating IRAK-4, assays will be performed to detect the effect of various compounds on IRAK-4 activity in a cell. Such assays can involve the identification of compounds that interact with IRAK-4 proteins, either physically or genetically, and can thus rely on any of a number of standard methods to detect physical or genetic interactions between compounds. Such assays can also involve the identification of compounds that affect IRAK-4 expression, activity or other properties, such as its phosphorylation or ability to bind other proteins. Such assays can also involve the detection of IRAK-4 activity in a cell, either in vitro or in vivo, and can thus involve the detection of, e.g., NF-κB activation using any standard assay, e.g., by measuring IκB levels, NF-κB nuclear localization, or the expression of natural or recombinant NF-κB target genes. Such cell-based assays can be performed in any type of cell, e.g., a cell that naturally expresses IRAK-4, or a cultured cell that produces IRAK-4 due to recombinant expression.

B. Assays for IRAK-4 Interacting Compounds

In certain embodiments, assays will be performed to identify molecules that physically or genetically interact with IRAK-4 proteins. Such molecules can be any type of molecule, including polypeptides, polynucleotides, amino acids, nucleotides, carbohydrates, lipids, or any other organic or inorganic molecule. Such molecules may represent molecules that normally interact with IRAK-4 to effect IL-1/Toll receptor signal transduction, or may be synthetic or other molecules that are capable of interacting with IRAK-4 and that can potentially be used to modulate IRAK-4 activity in cells, or used as lead compounds to identify classes of molecules that can interact with and/or modulate IRAK-4. Such assays may represent physical binding assays, such as affinity chromatography, immunoprecipitation, two-hybrid screens, or other binding assays, or may represent genetic assays as described infra.

In any of the binding or functional assays described herein, in vivo or in vitro, any IRAK-4 protein, or any derivative, variation, homolog, or fragment of an IRAK-4 protein, can be used. Preferably, the IRAK-4 protein is at least about 70% identical to SEQ ID NO:1 or 3. In numerous embodiments, a fragment of an IRAK-4 protein is used. For example, a fragment that contains only an N-terminal death domain, or a central kinase domain, can be used. Such fragments can be used alone, in combination with other IRAK-4 fragments, or in combination with sequences from heterologous proteins, e.g., the fragments can be fused to a heterologous polypeptide, thereby forming a chimeric polypeptide.

1. Assays for Physical Interactions

Compounds that interact with IRAK-4 proteins can be isolated based on an ability to specifically bind to a IRAK-4 protein or fragment thereof. In numerous embodiments, the IRAK-4 protein or protein fragment will be attached to a solid support. In one embodiment, affinity columns are made using the IRAK-4 polypeptide, and physically-interacting molecules are identified. It will be apparent to one of skill that chromatographic techniques can be performed at any scale and using equipment from many different manufacturers (e.g., Pharmacia Biotech). In addition, molecules that interact with IRAK-4 proteins in vivo can be identified by co-immunoprecipitation or other methods, i.e., immunoprecipitating IRAK-4 proteins using anti-IRAK-4 antibodies from a cell or cell extract, and identifying compounds, e.g., proteins, that are precipitated along with the IRAK-4 protein. Such methods are well known to those of skill in the art and are taught, e.g., in Ausubel, et al., Sambrook, et al., Harlow & Lane, all supra.

Two-hybrid screens can also be used to identify polypeptides that interact in vivo with an IRAK-4 polypeptide or a fragment thereof (Fields, et al., Nature 340:245–246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene typically encodes an easily detectable gene product, e.g., β-galactosidase, GFP, or luciferase, which can be detected using standard methods. In the present invention, an IRAK-4 polypeptide is fused to one of the two domains of the transcription factor, and the potential IRAK-4-binding polypeptides (e.g., encoded by a cDNA library) are fused to the other domain. Such methods are well known to those of skill in the art, and are taught, e.g., in Ausubel, et al., supra.

C. Assays for IRAK-4 Protein Activity

IRAK-4 genes and their alleles and polymorphic variants encode protein kinases that promote IL-1/Toll receptor signal transduction. Accordingly, the activity of IRAK-4 polypeptides can be assessed using a variety of in vitro and in vivo assays to determine functional, chemical, and physical effects, e.g., directly measuring the kinase activity of IRAK-4 using in vitro kinase assays, e.g., using IRAK-1 as a substrate, measuring the expression or activity of downstream effectors such as NF-kB or TRAF-6, measuring the binding of IRAK-4 to heterologous proteins, e.g., TRAF-6 or IRAK-1, or to other molecules (e.g., radioactive binding), measuring IRAK-4 protein and/or RNA levels, or measuring other aspects of IRAK-4 polypeptides, e.g., phosphorylation levels, transcription levels, and the like. Such assays can be used to test for both activators and inhibitors of IRAK-4 proteins. Modulators can also be genetically altered versions of IRAK-4 proteins, e.g., dominant negative forms of IRAK-4 or of proteins that interact with IRAK-4, e.g., IL-1RI, MyD88, and TRAF-6. Such modulators of activity are useful for, e.g., many diagnostic and therapeutic applications.

The IRAK-4 protein of the assay will typically be a recombinant or naturally occurring polypeptide with a sequence of SEQ ID NO:1 or 3 or conservatively modified variants thereof. Alternatively, the IRAK-4 protein of the assay will be derived from a eukaryote and include an amino acid subsequence having amino acid sequence identity to SEQ ID NO:1 or 3. Generally, the amino acid sequence identity will be at least 60%, optionally at least 70% to 85%, optionally at least 90–95%. Optionally, the polypeptide of the assays will comprise a domain of an IRAK-4 protein, such as an N-terminal death domain or a central kinase domain. In certain embodiments, a domain of an IRAK-4 protein, e.g., an N-terminal death domain or a central kinase domain, is bound to a solid substrate and used, e.g., to isolate any molecules that can bind to and/or modulate their activity. In certain embodiments, a domain of an IRAK-4 polypeptide, e.g., an N-terminal domain, a C-terminal domain, an extracellular loop, or one or more transmembrane domains, is fused to a heterologous polypeptide, thereby forming a chimeric polypeptide. Such chimeric polypeptides are also useful, e.g., in assays to identify modulators of IRAK-4.

Samples or assays that are treated with a potential IRAK-4 protein inhibitor or activator are compared to control samples without the test compound, to examine the extent of modulation. Control samples (untreated with activators or inhibitors) are assigned a relative IRAK-4 activity value of 100. Inhibition of an IRAK-4 protein is achieved when the IRAK-4 activity value relative to the control is about 90%, optionally 50%, optionally 25–0%. Activation of an IRAK-4 protein is achieved when the IRAK-4 activity value relative to the control is 110%, optionally 150%, 200–500%, or 1000–2000%.

The effects of the test compounds upon the function of the polypeptides can be measured by examining any of the parameters described above. Any suitable physiological change that affects IRAK-4 activity can be used to assess the influence of a test compound on the polypeptides of this invention. When the functional consequences are determined using intact cells or animals, one can also measure a variety of effects such as changes in inflammation of tissues, as indicated by, e.g., pain, heat, redness, swelling, loss of function, dilatation of arterioles, capillaries and venules, with increased permeability and blood flow, exudation of fluids, including plasma proteins and leucocytic migration into the site of inflammation.

In another embodiment, transcription levels can be measured to assess the effects of a test compound on IRAK-4 signal transduction. A host cell containing an IRAK-4 protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured using any method known to those of skill in the art to be suitable. For example, mRNA expression of the protein of interest may be detected using Northern blots or by detecting their polypeptide products using immunoassays. Any polynucleotide typically expressed following IRAK-4 activation can be used, i.e., any gene with an NF-κB cognate DNA binding site (see, e.g., Lenardo, et al., *Cell* 58:227 (1989); Grilli, et al., *Int. Rev. Cytol.* 143:1 (1993); Baeuerle, et al., *Ann. Rev. Immunol.* 12:141 (1994)). Such assays can use natural targets of NF-κB or can use reporter genes, e.g., chloramphenicol acetyltransferase, luciferase, β-galactosidase, GFP, and alkaline phosphatase, operably linked to a promoter containing an NF-κB binding site. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

D. Modulators and Binding Compounds

The compounds tested as modulators of an IRAK-4 protein can be any small chemical compound, or a biological entity, such as a protein, sugar, nucleic acid or lipid. Alternatively, modulators can be genetically altered versions of a IRAK-4 gene. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton, et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs, et al., *Proc. Nat. Acad. Sci. USA* 90:6909–6913 (1993)), vinylogous polypeptides (Hagihara, et al., *J. Amer. Chem. Soc.* 114:6568 (1992)), nonpeptidal peptidomimetics with glucose scaffolding (Hirschmann, et al., *J. Amer. Chem. Soc.* 114:9217–9218 (1992)), analogous organic syntheses of small compound libraries (Chen, et al., *J. Amer. Chem. Soc.* 116:2661 (1994)), oligocarbamates (Cho, et al., *Science* 261:1303 (1993)), and/or peptidyl phosphonates (Campbell, et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn, et al., *Nature Biotechnology*, 14(3):309–314 (1996) and PCT/US96/10287), carbohydrate libraries (see, e.g., Liang, et al., *Science*, 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

1. Solid State and Soluble High Throughput Assays

In one embodiment, the invention provides soluble assays using molecules such as an N-terminal or C-terminal domain either alone or covalently linked to a heterologous protein to create a chimeric molecule. In another embodiment, the invention provides solid phase based in vitro assays in a high throughput format, where a domain, chimeric molecule, IRAK-4 protein, or cell or tissue expressing an IRAK-4 protein is attached to a solid phase substrate.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen, et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon, et al., *Clinical Chemistry* 39(4):718–719 (1993); and Kozal, et al., *Nature Medicine* 2(7):753759 (1996) (all describing arrays of biopolymers fixed to solid substrates). Nonchemical approaches for fixing tag binders to substrates include other common methods, such as heat, cross-linking by UV radiation, and the like.

2. Computer-based Assays

Yet another assay for compounds that modulate IRAK-4 protein activity involves computer assisted drug design, in which a computer system is used to generate a three-dimensional structure of an IRAK-4 protein based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind. These regions are then used to identify compounds that bind to the protein.

The three-dimensional structural model of the protein is generated by entering protein amino acid sequences of at least 10 amino acid residues or corresponding nucleic acid sequences encoding an IRAK-4 polypeptide into the computer system. The nucleotide sequence encoding the polypeptide preferably comprises SEQ ID NO:2 or SEQ ID NO:4, and conservatively modified versions thereof. The amino acid sequence, preferably comprising SEQ ID NO:1 or 3, or conservatively modifies versions thereof, represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described above. The three-dimensional structure of the potential modulator is then compared to that of the IRAK-4 protein to identify compounds that bind to the protein. Binding affinity between the protein and compound is determined using energy terms to determine which compounds have an enhanced probability of binding to the protein.

Computer systems are also used to screen for mutations, polymorphic variants, alleles and interspecies homologs of IRAK-4 genes. Such mutations can be associated with disease states or genetic traits. As described above, Gene-Chip™ and related technology can also be used to screen for mutations, polymorphic variants, alleles and interspecies homologs. Once the variants are identified, diagnostic assays can be used to identify patients having such mutated genes. Identification of the mutated IRAK-4 genes involves receiving input of a first nucleic acid sequence of SEQ ID NO:2 or 4, or a first amino acid sequence of SEQ ID NO:1 or 3, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various IRAK-4 genes, and mutations associated with disease states and genetic traits.

VII. Modulating IRAK-4 Activity/Expression to Treat Diseases or Conditions.

In numerous embodiments of this invention, a compound, e.g., nucleic acid, polypeptide, or other molecule is administered to a patient, in vivo or ex vivo, to effect a change in IRAK-4 activity or expression in the patient. Such compounds can be nucleic acids encoding full length IRAK-4 polypeptides, e.g., as shown as SEQ ID NO:1 or 3, or any derivative, fragment, or variant thereof, operably linked to a promoter. Suitable nucleic acids also include inhibitory sequences such as antisense or ribozyme sequences, which can be delivered in, e.g., an expression vector operably linked to a promoter, or can be delivered directly. Also, any nucleic acid that encodes a polypeptide that modulates the expression of IRAK-4 can be used. In general, nucleic acids can be delivered to cells using any of a large number of vectors or methods, e.g., retroviral, adenoviral, or adeno-associated virus vectors, liposomal formulations, naked DNA injection, and others. All of these methods are well known to those of skill in the art.

Proteins can also be delivered to a patient to modulate IRAK-4 activity. In preferred embodiments, a polyclonal or monoclonal antibody that specifically binds to IRAK-4, particularly to an N-terminal death domain or a central kinase domain of an IRAK-4 polypeptide, will be delivered. In addition, any polypeptide that interacts with and/or modulates IRAK-4 activity can be used, e.g., a polypeptide that is identified using the presently described assays, or any dominant negative form of IRAK-4 or an IRAK-4-interacting protein, e.g., IL-1RI, MyD88, TRAF6, etc. In addition, polypeptides that affect IRAK-4 expression can be used.

Further, any compound that is found to or designed to interact with and/or modulate the activity of IRAK-4 can be used. For example, any compound that is found, using the methods described herein, to bind to or modulate the activity of IRAK-4 can be used.

Any of the above-described molecules can be used to increase or decrease the expression or activity of IRAK-4, or to otherwise affect the properties and/or behavior of IRAK-4 polypeptides or polynucleotides, e.g., stability, phosphorylation, kinase activity, interactions with other proteins, etc. The present compounds can thus be used to treat any of a number of diseases, including, but not limited to (a) pulmonary diseases and diseases of the airway including, but not limited to, Adult Respiratory Disease Syndrome (ARDS), Chronic Obstructive Pulmonary Disease (OPD), pulmonary fibrosis, interstitial lung disease, asthma, chronic cough, and allergic rhinitis; (b) transplantation; (c) autoimmune diseases including, but not limited to, rheumatoid arthritis, systemic lupus erythematosus, multiple sclerosis, and diabetes (e.g., type 1 diabetes mellitus); (d) cancer including, but not limited to, solid tumors, skin cancer, and lymphoma; (e) cardiovascular diseases including, but not limited to, stroke and atherosclerosis; (f) diseases of the central nervous system including, but not limited to, neurodegenerative diseases; (g) non-CD14 mediated sepsis; (h) osteoarthritis; (i) osteoporosis; (j) psoriasis and diseases of the skin including, but not limited to, rash and contact and atopic dermatitis; (k) inflammatory bowel disease (including, but not limited to, Crohn's disease and ulcerative colitis); (l) Behcet's syndrome; (m) ankylosing spondylitis; (n) sarcoidosis; (o) gout; (p) ophthalmic diseases and conditions; and (q) CD14 mediated sepsis.

A. Administration and Pharmaceutical Compositions

Administration of any of the present molecules can be achieved by any of the routes normally used for introducing a modulator compound into ultimate contact with the tissue to be treated. The modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. (1985)).

The IRAK-4 modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and nonaqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered, a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the compound at various concentrations, as applied to the mass and overall health of the subject. Administration can be accomplished via single or divided doses.

VIII. Transgenic Animals

Transgenic and chimeric nonhuman mammals and methods for generating them are described below. The mammals are useful, inter alia, for testing the function of IRAK-4 in vivo, to generate models for the study of inflammatory diseases and conditions, and for the development of potential treatments for IRAK-4 related inflammatory diseases and conditions.

Transgenic and chimeric nonhuman mammals are generated that contain cells that lack at least one functional endogenous allele for IRAK-4. A "chimeric animal" includes some cells that lack the functional IRAK-4 gene of interest and other cells that do not have the inactivated gene. A "transgenic animal," in contrast, is made up of cells that have all incorporated the specific modification which renders the IRAK-4 gene inactive or otherwise altered. While a transgenic animal is typically always capable of transmitting the mutant IRAK-4 gene to its progeny, the ability of a chimeric animal to transmit the mutation depends upon whether the inactivated gene is present in the animal's germ cells. The modifications that inactivate or otherwise alter the IRAK-4 gene can include, for example, insertions, deletions, or substitutions of one or more nucleotides. The modifications can interfere with transcription of the gene itself, with translation and/or stability of the resulting mRNA, or can cause the gene to encode an inactive or otherwise altered IRAK-4 polypeptide, e.g., an IRAK-4 polypeptide with modified binding properties or kinase activity.

The claimed methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, C A, Ed., *Transgenic Animal Technology: A Laboratory Handbook*, Academic Press, 1994.

In preferred embodiments, transgenic mice will be produced as described in Thomas, et al., (1999) *Immunol.* 163:978–84; Kanakaraj, et al. (1998) *J. Exp. Med.* 187: 2073–9; or Yeh, et al., (1997) *Immunity* 7:715–725.

Typically, a modified IRAK-4 gene is introduced, e.g., by homologous recombination, into embryonic stem cells (ES), which are obtained from preimplantation embryos and cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255–258. Subsequently, the transformed ES cell is combined with a blastocyst from a nonhuman animal, e.g., a mouse. The ES cells colonize the embryo and in some embryos form the germ line of the resulting chimeric animal. See, Jaenisch, *Science* 240: 1468–1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut, et al., *Nature* 385: 810–813 (1997).

Other methods for obtaining a transgenic or chimeric animal having a mutant IRAK-4 gene in its genome is to contact fertilized oocytes with a vector that includes a polynucleotide that encodes a modified, e.g., inactive, IRAK-4 polypeptide. In some animals, such as mice, fertilization is typically performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells.

Fertilized oocytes are typically cultured in vitro until a pre-implantation embryo is obtained containing about 16–150 cells. The 16–32 cell stage of an embryo is described as a morula, whereas pre-implantation embryos containing more than 32 cells are termed blastocysts. These embryos show the development of a blastocoel cavity, typically at the 64 cell stage. The presence of a desired IRAK-4 mutation in the cells of the embryo can be detected by methods known to those of skill in the art, e.g., Southern blotting, PCR, DNA sequencing, or other standard methods. Methods for culturing fertilized oocytes to the pre-implantation stage are described, e.g., by Gordon, et al. (1984) *Methods Enzymol.* 101:414; Hogan et al. *Manipulation of the Mouse Embryo: A Laboratory Manual*, C.S.H.L. N.Y. (1986) (mouse embryo); Hammer, et al., *Nature* 315:680 (1985) (rabbit and porcine embryos); Gandolfi, et al., *J. Reprod. Fert.* 81:23–28 (1987); Rexroad, et al., *J Anim. Sci.* 66: 947–953 (1988) (ovine embryos) and Eyestone, et al., *J. Reprod. Fert.* 85:715–720 (1989); Camous, et al, *J. Reprod. Fert.* 72:779–785 (1984); and Heyman, et al., *Theriogenology* 27:5968 (1987) (bovine embryos). Pre-implantation embryos may also be stored frozen for a period pending implantation.

Pre-implantation embryos are transferred to an appropriate female resulting in the birth of a transgenic or chimeric animal, depending upon the stage of development when the transgene is integrated. Chimeric mammals can be bred to form true germline transgenic animals. Chimeric mice and germline transgenic mice can also be ordered from commercial sources (e.g., Deltagen, San Carlos, Calif.).

Other methods for introducing mutations into mammalian cells or animals include recombinase systems, which can be employed to delete all or a portion of a locus of interest. Examples of recombinase systems include, the cre/lox system of bacteriophage P1 (see, e.g., Gu, et al., *Science* 265:103–106 (1994); Terry, et al., *Transgenic Res.* 6:349–356 (1997)) and the FLP/FRT site specific integration system (see, e.g., Dymecki, *Proc. Natl. Acad. Sci. USA* 93:6191–6196 (1996)). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the IRAK-4 gene of interest, e.g., by using a tissue specific promoter to drive the expression of the recombinase. See, e.g., Tsien, et al., *Cell* 87:1317–26 (1996); Brocard, et al., *Proc. Natl. Acad. Sci. USA* 93:10887–10890 (1996); Wang, et al., *Proc. Natl. Acad. Sci. USA* 93:3932–6 (1996); Meyers, et al., *Nat. Genet.* 18:136–41 (1998)).

The presence of any mutation in an IRAK-4 gene in a cell or animal can be detected using any method described herein, e.g., Southern blot, PCR, or DNA sequencing. See, e.g., Ausubel, et al., supra.

IX. Kits

IRAK-4 genes and their homologs are useful tools for a number of applications, including, but not limited to, identifying IL-1, IL-18, or LPS-responsive cells, for forensics and paternity determinations, and for treating any of a large number of IL-1, IL-18, or LPS-associated diseases, such as inflammatory diseases. IRAK-4 specific reagents that specifically hybridize to IRAK-4 nucleic acids, such as IRAK-4 probes and primers, and IRAK-4 specific reagents that specifically bind to or modulate the activity of a IRAK-4 protein, e.g., IRAK-4 antibodies or other compounds can thus be provided in a kit for the practice of any of the applications described herein.

Nucleic acid assays for the presence of DNA and RNA for a IRAK-4 polynucleotide in a sample include numerous techniques known to those skilled in the art, such as Southern analysis, Northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer, et al., *Biotechniques* 4:230–250 (1986); Haase, et al., *Methods in Virology*, vol. VII, pp. 189–226 (1984); and *Nucleic Acid Hybridization: A Practical Approach* (Hames et al., eds. 1987). In addition, an IRAK-4 protein can be detected with the various immunoassay techniques described above. The test sample is typically compared to both a positive control (e.g., a sample expressing a recombinant IRAK-4 protein) and a negative control.

The present invention also provides kits for screening for modulators of IRAK-4 proteins or nucleic acids. Such kits can be prepared from readily available materials and reagents. For example, such kits can comprise any one or more of the following materials: IRAK-4 nucleic acids or proteins, reaction tubes, and instructions for testing IRAK-4 activity. Optionally, the kit contains a biologically active IRAK-4 protein. A wide variety of kits and components can be prepared according to the present invention, depending upon the intended user of the kit and the particular needs of the user.

X. Examples

A. Identification of Human IRAK-4

Sequences related to human IRAK (Cao, et al., *Science* 271:1128–31 (1996)) were identified in the sequence database (Genbank) at the National Center for Biotechnology Information using the TFASTX program of the Wisconsin Package Version 9.1 (Genetics Computer Group (GCG), Madison, Wis.). A human cDNA sequence (accession number AF155118) was found that encodes a polypeptide sharing significant homology with IRAK. A full length cDNA clone was amplified from a cDNA library (Clontech Universal Quick Clone cDNA) with a PCR reaction using a sense primer with the sequence ATGAACAAACCCATAA-CACCATCAACATATGTGC (SEQ ID NO: 5) and an antisense primer with the sequence TTAAGAAGCTGT-CATCTCTTGCAGC (SEQ ID NO: 6). The nucleotide sequence of this cDNA was determined with the Sanger method of dideoxy-mediated chain termination. The human IRAK-4 cDNA (see, e.g., SEQ ID NO:2) encodes a protein (see, e.g., SEQ ID NO:1) of 460 amino acids and a calculated molecular mass of 52 kDa. Analysis of the deduced protein sequence revealed an N-terminal death domain (Feinstein, et al., *Trends Biochem. Sci.* 20:342–4 (1995)) and a central kinase domain, similar to the domain structures of IRAK, IRAK-2 and IRAK-M (Wesche, et al., *J. Biol. Chem.* 274:19403–10 (1999)). The overall sequence identity shared between the newly identified protein and the existing IRAK-like molecules is between 30 to 40% (Table 1).

TABLE 1

Sequence similarities of human IRAK-4 to members of the IRAK/Pelle family. Sequence comparisons were performed using the GAP program of the Wisconsin GCG package.

|   | sequence identity | sequence similarity |
|---|---|---|
| IRAK | 36% | 48% |
| IRAK-2 | 28% | 39% |
| IRAK-M | 31% | 41% |
| Pelle | 30% | 40% |

B. Expression Pattern of Human IRAK-4

The expression pattern of human IRAK-4 was determined by Northern blot analysis using samples representing a variety of human tissues. Two mRNA species were detected, with sizes of approximately 4.4 kb and 3 kb. IRAK-4 expression was detected in thymus, spleen, kidney and liver.

Using RT-PCR to amplify human IRAK-4 RNA from various tissues, an amplification product was readily detectable in placenta, lung, liver, kidney, pancreas, prostate, testis, ovary, small intestine, colon, lymph node and tonsil.

C. IRAK-4 Activates NF-κB

Transient overexpression of human IRAK-4 was induced in the human, embryonic kidney cell line 293. As detected by reporter assays, this overexpression was found to lead to the activation of the transcription factor NF-κB in the cells. The reporter construct used in these assays was the NF-kB dependent E-selecting-luciferase reporter gene plasmid pELAM-luc (Schindler and Baichwal, (1994) *Mol. Cell Biol.*, 14:5820–31). Luciferase activity was determined using the luciferase assay system (Promega), as described in Wesche, et al., *Immunity* 7:837–47 (1997).

Overexpression of a IRAK-4 mutant that lacks kinase activity (IRAK-4 KK213AA, a mutation that removes a critical lysine residue in the ATP binding pocket), or of a truncated form of IRAK-4 (aa 1 . . . 191, consisting of only the first 191 amino acids), were found to act in a dominant negative manner to block the NF-κB activation induced by interleukin-1. These altered forms of IRAK-4, however, had no effect on NF-κB activation induced by TNF (as assayed in HEK 293 cells, using reporter assays).

D. Identification of Mouse IRAK-4

To identify murine IRAK-4 homologs, a murine kidney cDNA phage library (Clontech) was screened with a probe derived from a truncated human IRAK-4 (comprising nucleotides 1–992) under low stringency conditions according to standard procedures. One cDNA clone encoding an ORF with about 80% homology (at the protein level) to human IRAK-4 was identified. To obtain full length mIRAK-4, this clone was used to screen the same library under high stringency conditions. Several positive clones were identified, encoding overlapping fragments of mIRAK-4.

The murine IRAK-4 cDNA (see, e.g., SEQ ID NO: 4) encodes a 459 amino acid protein (see, e.g., SEQ ID NO:3) with a calculated molecular mass of 51 kDa, which shares 87% similarity and 84% identity with human IRAK-4 protein (analyzed with the GAP utility of the GCG package).

E. IL-1 Induced Association of IRAK-4 with TRAF6 and IRAK-1

Methods:

HEK 293 cells stably expressing IL-1RI (293RI, $1.5 \times 10^8$ cells per sample; (Cao, et al., *Science* 271:1128–31 (1996); Cao, et al., *Nature* 383:443–6 (1996)) were stimulated for 0, 2, 10 and 30 minutes with 100 ng/ml interleukin-1. The cells were collected, lysed for 20 min on ice in lysis buffer and centrifuged to remove cellular debris as described elsewhere (Wesche, et al., *Immunity* 7:837–47 (1997)). The cleared lysates were incubated with Protein-G beads (Pharmacia) and either a pre immune serum or a rabbit antiserum raised against *E. coli*-expressed, full length IRAK-4 for 24 h at four degrees centigrade. The immunoprecipitates were washed thoroughly, fractionated by SDS-PAGE, transferred to PVDF membranes and blotted with antisera raised against TRAF6 (Cao, et al., *Nature* 383:443–6 (1996)), IRAK-1 (Cao, et al., *Science* 271:1128–31 (1996)) or IRAK-4.

Result:

To address the involvement of IRAK-4 in IL-1 signaling, the ability of endogenous IRAK-4 to interact in an IL-1 dependent manner with known transducers of the IL-1 signal was analyzed. Lysates of 293RI cells stimulated with interleukin-1 for various lengths of time were immunoprecipitated with an antiserum against IRAK-4 and immunoblotted with antisera against IRAK-1 and TRAF6. IL-1 induced association of IRAK-4 with IRAK-1 and TRAF6 was observed at the earliest time point tested (two minutes), was increased after 10 min of incubation, and decreased after 30 min, showing an IL-1 induced, rapid and transient interaction of IRAK-4 with IRAK-1 and TRAF6, consistent with a role as an important molecule transducing the IL-1 signal. (See, e.g., FIG. 5.)

The absence of any IRAK-1 or TRAF6 signal in the samples precipitated with pre-immune serum demonstrates the specificity of the interaction, and the control blot with an IRAK-4 antiserum shows that equal amounts were precipitated.

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. An isolated IRAK-4 polypeptide comprising the amino acid sequence of SEQ ID NO:1.

2. An isolated IRAK-4 polypeptide comprising the amino acid sequence of SEQ ID NO:1, wherein the polypeptide comprises a substitution of alanine for lysine at residues 213 and 214 of SEQ ID NO:1.

3. An isolated IRAK-4 polypeptide, wherein the polypeptide consists of amino acids 1–191 of SEQ ID NO:1.

* * * * *

SEQUENCE LISTING

```
<160> NUMBER OF SEQ ID NOS: 7

<210> SEQ ID NO 1
<211> LENGTH: 460
<212> TYPE: PRT
<213> ORGANISM: Homo sapiens

<400> SEQUENCE: 1

Met Asn Lys Pro Ile Thr Pro Ser Thr Tyr Val Arg Cys Leu Asn Val
  1               5                  10                  15

Gly Leu Ile Arg Lys Leu Ser Asp Phe Ile Asp Pro Gln Glu Gly Trp
             20                  25                  30

Lys Lys Leu Ala Val Ala Ile Lys Lys Pro Ser Gly Asp Asp Arg Tyr
         35                  40                  45
```

-continued

```
Asn Gln Phe His Ile Arg Arg Phe Glu Ala Leu Leu Gln Thr Gly Lys
        50                  55                  60

Ser Pro Thr Ser Glu Leu Leu Phe Asp Trp Gly Thr Thr Asn Cys Thr
 65                  70                  75                  80

Ala Gly Asp Leu Val Asp Leu Leu Ile Gln Asn Glu Phe Phe Ala Pro
                 85                  90                  95

Ala Ser Leu Leu Leu Pro Asp Ala Val Pro Lys Thr Ala Asn Thr Leu
                100                 105                 110

Pro Ser Lys Glu Ala Ile Thr Val Gln Gln Lys Gln Met Pro Phe Cys
            115                 120                 125

Asp Lys Asp Arg Thr Leu Met Thr Pro Val Gln Asn Leu Glu Gln Ser
        130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
                165                 170                 175

Thr Asn Asn Phe Asp Glu Arg Pro Ile Ser Val Gly Gly Asn Lys Met
                180                 185                 190

Gly Glu Gly Gly Phe Gly Val Val Tyr Lys Gly Tyr Val Asn Asn Thr
            195                 200                 205

Thr Val Ala Val Lys Lys Leu Ala Ala Met Val Asp Ile Thr Thr Glu
        210                 215                 220

Glu Leu Lys Gln Gln Phe Asp Gln Glu Ile Lys Val Met Ala Lys Cys
225                 230                 235                 240

Gln His Glu Asn Leu Val Glu Leu Leu Gly Phe Ser Ser Asp Gly Asp
                245                 250                 255

Asp Leu Cys Leu Val Tyr Val Tyr Met Pro Asn Gly Ser Leu Leu Asp
                260                 265                 270

Arg Leu Ser Cys Leu Asp Gly Thr Pro Pro Leu Ser Trp His Met Arg
            275                 280                 285

Cys Lys Ile Ala Gln Gly Ala Ala Asn Gly Ile Asn Phe Leu His Glu
        290                 295                 300

Asn His His Ile His Arg Asp Ile Lys Ser Ala Asn Ile Leu Leu Asp
305                 310                 315                 320

Glu Ala Phe Thr Ala Lys Ile Ser Asp Phe Gly Leu Ala Arg Ala Ser
                325                 330                 335

Glu Lys Phe Ala Gln Thr Val Met Thr Ser Arg Ile Val Gly Thr Thr
            340                 345                 350

Ala Tyr Met Ala Pro Glu Ala Leu Arg Gly Glu Ile Thr Pro Lys Ser
        355                 360                 365

Asp Ile Tyr Ser Phe Gly Val Val Leu Leu Glu Ile Ile Thr Gly Leu
    370                 375                 380

Pro Ala Val Asp Glu His Arg Glu Pro Gln Leu Leu Leu Asp Ile Lys
385                 390                 395                 400

Glu Glu Ile Glu Asp Glu Glu Lys Thr Ile Glu Asp Tyr Ile Asp Lys
                405                 410                 415

Lys Met Asn Asp Ala Asp Ser Thr Ser Val Glu Ala Met Tyr Ser Val
            420                 425                 430

Ala Ser Gln Cys Leu His Glu Lys Lys Asn Lys Arg Pro Asp Ile Lys
        435                 440                 445

Lys Val Gln Gln Leu Leu Gln Glu Met Thr Ala Ser
450                 455                 460
```

-continued

<210> SEQ ID NO 2
<211> LENGTH: 1383
<212> TYPE: DNA
<213> ORGANISM: Homo sapiens
<220> FEATURE:
<223> OTHER INFORMATION: human IL-1 receptor-associated kinase 4
      (IRAK-4) cDNA
<220> FEATURE:
<221> NAME/KEY: CDS
<222> LOCATION: (1)..(1383)
<223> OTHER INFORMATION: human IRAK-4

<400> SEQUENCE: 2

```
atgaacaaac ccataacacc atcaacatat gtgcgctgcc tcaatgttgg actaattagg      60
aagctgtcag attttattga tcctcaagaa ggatggaaga gttagctgt agctattaaa     120 aaaccatctg gtgatgatag atacaatcag tttcacataa ggagatttga agcattactt    180
caaactggaa aaagtcccac ttctgaatta ctgtttgact ggggcaccac aaattgcaca    240
gctggtgatc ttgtggatct tttgatccaa atgaattttt ttgctcctgc gagtcttttg    300
ctcccagatg ctgttcccaa aactgctaat acactacctt ctaaagaagc tataacagtt    360
cagcaaaaac agatgccttt ctgtgacaaa gacaggacat tgatgacacc tgtgcagaat    420
cttgaacaaa gctatatgcc acctgactcc tcaagtccag aaaataaaag tttagaagtt    480
agtgatacac gttttcacag ttttttcattt tatgaattga gaatgtcac aaataacttt    540 gatgaacgac ccatttctgt tggtggtaat aaaatgggag agggaggatt tggagttgta    600
tataaaggct acgtaaataa cacaactgtg gcagtgaaga agcttgcagc aatggttgac    660
attactactg aagaactgaa acagcagttt gatcaagaaa taaagtaat ggcaaagtgt    720 caacatgaaa acttagtaga actacttggt ttctcaagtg atggagatga cctctgctta    780
gtatatgttt acatgcctaa tggttcattg ctagacagac tctcttgctt ggatggtact    840
ccaccacttt cttggcacat gagatgcaag attgctcagg gtgcagctaa tggcatcaat    900
tttctacatg aaaatcatca tattcataga gatattaaaa gtgcaaatat cttactggat    960
gaagctttta ctgctaaaat atctgacttt ggccttgcac gggcttctga aagtttgcc   1020 cagacagtca tgactagcag aattgtggga acaacagctt atatggcacc agaagctttg   1080
cgtggagaaa taacacccaa atctgatatt tacagctttg gtgtggtttt actagaaata   1140
ataactggac ttccagctgt ggatgaacac cgtgaacctc agttattgct agatattaaa   1200
gaagaaattg aagatgaaga aaagacaatt gaagattata ttgataaaaa gatgaatgat   1260
gctgattcca cttcagttga agctatgtac tctgttgcta gtcaatgtct gcatgaaaag   1320
aaaaataaga gaccagacat taagaaggtt caacagctgc tgcaagagat gacagcttct   1380
taa                                                                1383
```

<210> SEQ ID NO 3
<211> LENGTH: 459
<212> TYPE: PRT
<213> ORGANISM: Mus sp.

<400> SEQUENCE: 3

```
Met Asn Lys Pro Leu Thr Pro Ser Thr Tyr Ile Arg Asn Leu Asn Val
  1               5                  10                  15

Gly Ile Leu Arg Lys Leu Ser Asp Phe Ile Asp Pro Gln Glu Gly Trp
             20                  25                  30

Lys Lys Leu Ala Val Ala Ile Lys Lys Pro Ser Gly Asp Asp Arg Tyr
         35                  40                  45
```

```
Asn Gln Phe His Ile Arg Arg Phe Glu Ala Leu Leu Gln Thr Gly Lys
 50                  55                  60

Ser Pro Thr Cys Glu Leu Leu Phe Asp Trp Gly Thr Thr Asn Cys Thr
 65                  70                  75                  80

Val Gly Asp Leu Val Asp Leu Leu Val Gln Ile Glu Leu Phe Ala Pro
                 85                  90                  95

Ala Thr Leu Leu Leu Pro Asp Ala Val Pro Gln Thr Val Lys Ser Leu
                100                 105                 110

Pro Pro Arg Glu Ala Ala Thr Val Ala Gln Thr His Gly Pro Cys Gln
            115                 120                 125

Glu Lys Asp Arg Thr Ser Val Met Pro Met Pro Lys Leu Glu His Ser
        130                 135                 140

Cys Glu Pro Pro Asp Ser Ser Pro Asp Asn Arg Ser Val Glu Ser
145                 150                 155                 160

Ser Asp Thr Arg Phe His Ser Phe Ser Phe His Glu Leu Lys Ser Ile
                165                 170                 175

Thr Asn Asn Phe Asp Glu Gln Pro Ala Ser Ala Gly Gly Asn Arg Met
                180                 185                 190

Gly Glu Gly Gly Phe Gly Val Val Tyr Lys Gly Cys Val Asn Asn Thr
            195                 200                 205

Ile Val Ala Val Lys Lys Leu Gly Ala Met Val Glu Ile Ser Thr Glu
            210                 215                 220

Glu Leu Lys Gln Gln Phe Asp Gln Glu Ile Lys Val Met Ala Thr Cys
225                 230                 235                 240

Gln His Glu Asn Leu Val Glu Leu Leu Gly Phe Ser Ser Asp Ser Asp
                245                 250                 255

Asn Leu Cys Leu Val Tyr Ala Tyr Met Pro Asn Gly Ser Leu Leu Asp
                260                 265                 270

Arg Leu Ser Cys Leu Asp Gly Thr Pro Pro Leu Ser Trp His Thr Arg
            275                 280                 285

Cys Lys Val Ala Gln Gly Thr Ala Asn Gly Ile Arg Phe Leu His Glu
        290                 295                 300

Asn His His Ile His Arg Asp Ile Lys Ser Ala Asn Ile Leu Leu Asp
305                 310                 315                 320

Lys Asp Phe Thr Ala Lys Ile Ser Asp Phe Gly Leu Ala Arg Ala Ser
                325                 330                 335

Ala Arg Leu Ala Gln Thr Val Met Thr Ser Arg Ile Val Gly Thr Thr
            340                 345                 350

Ala Tyr Met Ala Pro Glu Ala Leu Arg Gly Glu Ile Thr Pro Lys Ser
        355                 360                 365

Asp Ile Tyr Ser Phe Gly Val Val Leu Leu Glu Leu Ile Thr Gly Leu
    370                 375                 380

Ala Ala Val Asp Glu Asn Arg Glu Pro Gln Leu Leu Leu Asp Ile Lys
385                 390                 395                 400

Glu Glu Ile Glu Asp Glu Glu Lys Thr Ile Glu Asp Tyr Thr Asp Glu
                405                 410                 415

Lys Met Ser Asp Ala Asp Pro Ala Ser Val Glu Ala Met Tyr Ser Ala
            420                 425                 430

Ala Ser Gln Cys Leu His Glu Lys Lys Asn Arg Arg Pro Asp Ile Ala
        435                 440                 445

Lys Val Gln Gln Leu Leu Gln Glu Met Ser Ala
    450                 455
```

<210> SEQ ID NO 4
<211> LENGTH: 1542
<212> TYPE: DNA
<213> ORGANISM: Mus sp.
<220> FEATURE:
<223> OTHER INFORMATION: murine IL-1 receptor-associated kinase 4
      (IRAK-4) cDNA
<220> FEATURE:
<221> NAME/KEY: CDS
<222> LOCATION: (163)..(1542)
<223> OTHER INFORMATION: murine IRAK-4

<400> SEQUENCE: 4

```
gcggccgcgt cgacatgccc cggtgacccg cagcatcccg atcgcaggca gtctgaagtc    60
gcctggtggt cctgcgtcct ccaccccga gtcctcgccg acgtggcgg acgccgatc     120 gccttgtcca ggaagcgagg acgtccgag aggaagtaga agatgaacaa gccgttgaca   180
ccatcgacat acatacgcaa ccttaatgtg gggatcctta ggaagctgtc ggatttttatt 240 gatcctcaag aagggtggaa gaaattagca gtagctatca aaaagccgtc cggcgacgac  300
agatacaatc agttccatat aaggagattc gaagccttac ttcagaccgg aagagcccc   360 acctgtgaac tgctgtttga ctgggcacc acgaactgca cagttggcga ccttgtggat   420
ctactggtcc agattgagct gttttgcccc gccactctcc tgctgccgga tgccgttccc  480
caaaccgtca aaagcctgcc tcctagagaa gcggcaacag tggcacaaac acgggcct    540 tgtcaggaaa aggacaggac atccgtaatg cctatgccga agctagaaca cagctgcgag  600
ccaccggact cctcaagccc agacaacaga agtgtagagt ccagcgacac tcggttccac  660
agcttctcgt tccatgaact gaagagcatc acaaacaact tcgacgagca acccgcgtct  720
gccggtggca accggatggg gagggggga tttggagtgg tgtacaaggg ctgtgtgaac   780
aacaccatcg tggcggtgaa gaagctcgga gcgatggttg aaatcagtac tgaagaacta  840
aagcaacagt ttgatcaaga aattaaagta atggcaacgt gtcagcacga aacctggtg   900 gagctgctcg gcttctccag cgacagcgac aacctgtgct tagtgtatgc ttacatgccc  960
aacgggtcct gctggacag actgtcctgc ctggatggta caccaccgct ttcctggcac  1020
acaaggtgca aggttgctca ggggacagca atggcatca ggtttctgca tgaaaatcat  1080
cacattcata gagatattaa aagtgcaaat atcttactag acaaagactt tactgccaaa  1140
atatctgact ttgggcttgc acgggcttcg gcaaggctag cgcagacggt catgaccagc  1200
cgaatcgtgg gcacaacggc ttacatggca cccgaagctt gcggggaga ataacaccc   1260 aaatctgaca tctacagctt cggcgtggtt ctgttggagc tgataaccgg gctggcggct  1320
gtggatgaaa accgtgaacc tcaactactg ctggatatta agaagagat tgaagatgaa   1380 gagaagacga ttgaagatta cacggatgag aagatgagcg atgcggaccc tgcttcggtg  1440
gaagcaatgt actctgctgc tagccagtgt ctgcatgaga agaaaaacag acggccagac  1500
attgcaaagg ttcaacagct gctacaagag atgtctgctt aa                    1542
```

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:sense primer
      for amplification of human IRAK-4

<400> SEQUENCE: 5
atgaacaaac ccataacacc atcaacatat gtgc                              34

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:antisense
      primer for amplification of human IRAK-4

<400> SEQUENCE: 6
ttaagaagct gtcatctctt gcagc                                      25

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:epitope tag

<400> SEQUENCE: 7

Asp Tyr Lys Asp Asp Asp Asp Lys
 1               5
```